(12) United States Patent
Yang et al.

(10) Patent No.: US 6,810,140 B2
(45) Date of Patent: Oct. 26, 2004

(54) THREE DIMENSIONAL REAL-TIME IMAGE APPARATUS OF OCULAR RETINA

(75) Inventors: Yunsik Yang, Icksan (KR); Sungki Lyu, Jinju (KR)

(73) Assignee: Research Center for Aircraft Parts Technology, Kyungsangnam-do (KR)

( * ) Notice: Subject to any disclaimer, the term of this patent is extended or adjusted under 35 U.S.C. 154(b) by 588 days.

(21) Appl. No.: 09/803,654

(22) Filed: Mar. 12, 2001

(65) Prior Publication Data

US 2001/0022850 A1 Sep. 20, 2001

(30) Foreign Application Priority Data

Mar. 16, 2000 (KR) .......................................... 2000-13377

(51) Int. Cl.[7] .................................................. G06K 9/00

(52) U.S. Cl. ........................ 382/154; 382/128; 351/240

(58) Field of Search ................................ 382/154, 128; 351/210, 221, 240; 356/627

(56) References Cited

U.S. PATENT DOCUMENTS

| | | | | |
|---|---|---|---|---|
| 5,202,711 A | * | 4/1993 | Klingbeil | 351/224 |
| 5,355,181 A | * | 10/1994 | Ashizaki et al. | 348/744 |
| 5,430,509 A | * | 7/1995 | Kobayashi | 351/221 |
| 5,627,613 A | * | 5/1997 | Kaneko | 351/221 |
| 5,847,805 A | * | 12/1998 | Kohayakawa et al. | 351/210 |

OTHER PUBLICATIONS

Ciulla, T.A., "Three–Dimensional Retinal Imaging", *Review of Opthalmology*.
Stephenson, M. "Retinal thickness analysis may aid in early detection of glaucoma", *Glaucoma*.
Geronimo, F.D. et al. "A quantitative in vivo study of retinal thickness before and after laser treatment for macular edema due to retinal vein occlusion", *Euro. J. Ophthal.*, vol. 11(2) pp. 145–149.
Roorda, A. et al. "Adaptive optics scanning laser opthalmoscopy", *Optics Express*, vo.10(9) pp. 405–412, 2002.
Campbell, M. et al., "Confocal Scanning Laser Ophthalmology", *Confocal Scanning Laser Opthalmoscope*, Abstract.
Nagpal, M. et al. "Scanning Laser Opthalmoscopy in Macular Degeneration".

(List continued on next page.)

*Primary Examiner*—Leo Boudreau
*Assistant Examiner*—Ryan J. Miller
(74) *Attorney, Agent, or Firm*—Nath & Associates PLLC; Gary M. Nath; Lee C. Heiman

(57) ABSTRACT

The disclosed content relates to a three dimensional real-time imaging apparatus of the ocular retina, which is associated with the most frequent ophthalmic diseases. In the present invention, the laser rays are formed into two dimensional ray surface sequentially with the time by using a polygon mirror motor and galvanometer and irradiated on the almost transparent retina through the pupil. The optical system is so arranged that the incident angles, relative to a retina, of the laser beams irradiated on the retina at respective moments may agree with the output angles of imaginary lines of the same laser rays reflected from a retina in both the vertical and horizontal direction. Further, the laser sequential single lines lit on the retina are caused to correspond to the sensors array, so that two dimensional retinal surface elements as many as the sensors of the sensor array are imaged in real time three dimensions. Accordingly, this type of apparatus permits the observation of retinal images in real time three dimensions, which was not possible with conventional apparatuses. In addition, three dimensional inspection of eye-ground, sensitive imaging of various retinal diseases and detailed evaluation of the responses to various treatments are possible, so that an epochal assistance can be given to the understanding of retinal diseases and the development of the therapeutic methods.

3 Claims, 9 Drawing Sheets

OTHER PUBLICATIONS

Nejadmalayeri, A. H. "Optical Coherence Tomography", Dec. 14, 2001.

Steele, C. "Optical coherence Tomography: Managing diabetic retinopathy", *Clinical*, Jul. 11, 2003.

Ang, A. "Improvement of reproducibility of macular volume measurements using the Heidelberg retinal tomograph", *Br J Opthalmol*, vol. 84 pp. 1194–1197, 2000.

Agarwal, H.C. et al. "The normal optic nerve head on Heidelberg Retina Tomograph II", *Indian J. Opthalmol*, vol. 51 pp. 25–33, 2003, Abstract.

Ahn, J.K. "Morphometric change analysis of the optic nerve head in unilateral disk hemorrhage cases", *Am J Ophthalmol*, vol. 134 pp. 920–922, 2002, Abstract.

Akiba, J. "Three–dimensional characteristics of macular pseudoholes using confocal laser tomography", *Opthalmic Surg Lasers*, vol. 30 pp. 513–517, 1999, Abstract.

Ang, A. et al. "Improvement of reproducibility of macular volume measurements using the Heidelberg retinal tomograph", *Br J Ophthalmol*, vol. 84 pp. 1194–1197, 2000, Abstract.

Anton, A. et al. "Mapping structural to functional damage in glaucoma with standard automated perimetry and confocal scanning laser opthalmoscopy", Am J Ophthalmol, vol. 125 pp. 436–446, 1998, Abstract.

Anton, A. et al. "[New parameters for the detection and location of focal damage in glaucoma.] Neuvos parametros para la deteccion y localizacion de dano focal en el glaucoma", *Arch Soc Esp Oftalmol*, vol. 73 pp. 431–438, 1998, Abstract.

Anton, A. "Optic nerve assessment: A clinical endpoint of optic neuropathy", Eur J Ophthalmol, 9 Suppl 1: S37–39, 1999, Abstract.

Anton, A. "Measuring structural changes in the optic nerve head and retinal nerve fibre layer", Eur J Ophthalmol, 11 Suppl 2:S50–S56, 2001, Abstract.

Arvas, S. et al. "The capillary blood flow in ischaemic type central retinal vein occlusion: the effect of laser photocoagulation", *Acta Opthalmol Scand*, vol. 80 pp. 490–494, 2002, Abstract.

Asawaphureekorn, S. "Ranked–segment distribution curve for interpretation of optic nerve topography", *J Glaucoma*, vol. 5 pp. 79–90, 1996, Abstract.

Aung, T. et al. "The phenotype of normal tension glaucoma patients with and without OPA1 polymorphisms", *Br J Ophthalmol*, vol. 87 pp. 149–152, 2003, Abstract.

Azuara–Blanco, A. et al. "Methods to objectify reversibility of glaucomatous cupping", *Curr Opin Ophthalmol*, vol. 8 pp. 50–54, 1997, Abstract.

Azuara–Blanco, A. et al. "Effects of short term increase of intraocular pressure on optic disc cupping", *Br J Ophthalmol*, vol. 82 pp. 880–883, 1998, Abstract.

Azuara–Blanco, A. et al. "Reproducibility of optic disk topographic measurements with the Topcon ImageNet and the Heidelberg Retina Tomograph", *Ophthalmologica*, vol. 212 pp. 95–98, 1998, Abstract.

Azuara–Blanco, A. et al. "Comparison between laser scanning tomography and computerised image analysis of the optic disc.", *Br J Ophthalmol*, vol. 83 pp. 295–298, 1998, Abstract.

Bartsch, D.U. et al. "Laser–tissue interaction and artifacts in confocal scanning laser ophthalmoscopy and tomography", *Neurosci Biobehav Rev*, vol. 17 pp. 459–467, 1993, Abstract.

Bartsch, D.U. et al. "Axial intensity distribution analysis of the human retina with a confocal scanning laser tomograph", *Exp Eye Res*, vol. 58 pp. 161–173, 1994, Abstract.

Bartz–Schmidt K.U. et al. Validity of two dimensional data obtained with the Heidelberg Retina Tomograph as verified by direct measurements in normal optic nerve heads, *Ger J Ophthalmol*, vol. 3 pp. 400–405, 1994, Abstract.

Bartz–Schmidt K.U. et al. "The normalized rim/disc area ratio line", *Int Ophthalmol*, vol. 19 pp. 331–335, 1995, Abstract.

Bartz–Schmide K.U. et al. "The cumulative normalised rim/disc area ratio curve", *Graefes Arch Clin Exp Ophthalmol*, vol. 234 pp. 227–231, 1996, Abstract.

Bartz–Schmidt K.U. et al. "[Effect of the contour line on cup surface using the Heidelberg Retina Tomograph.] Zum Einfluβ der Konturlinie auf die Exkavationsfläche beim Heidelberg Retina Tomograph", *Klin* Monatsbl Augenheilkd, vol. 209 pp. 292–297, 1996, Abstract.

Bartz–Schmidt K.U. et al. "Quantitative morphologic and functional evaluation of the optic nerve head in chronic open–angle glaucoma", *Surv Ophthalmol*, vol. 44 (Suppl 1) pp. S41–S53, 1999, Abstract.

Bathija, R. et al. "Detection of early glaucomatous structural damage with confocal laser scanning tomography", *J Glaucoma*, vol. 7 pp. 121–127, 1998, Abstract.

Bayer, A. et al. "Validity of a new disk grading scale for estimating glaucomatous damage: correlation with visual field damage", *Am J Ophthalmol*, vol. 133 pp. 758–763, 2002, Abstract.

Beatty, S. et al. "Evaluation of optic disc cupping using high–resolution ocular ultrasound", Eye, vol. 12 pp. 54–60, 1998, Abstract.

Beatty, S. et al. "Correlation between the orbital and intraocular portions of the optic nerve in glaucomatous and ocular hypertensive eyes", Eye, vol. 12 pp. 707–713, 1998, Abstract.

Blumenthal, E.Z.et al. "Assessment of the retinal nerve fiber layer in clinical trials of glaucoma neuroprotection", *Surv. Ophthalmol*, vol. 45 Suppl 3 pp. S305–312, 2001, Abstract.

Borges, K.F. "[Stereometric analysis of the optic disc with Heidelberg Retina Tomography in normal tension glaucoma patients.] Analise esteriometrica do disco optico com Heidelberg Retina Tomograph (HRT) em paceientes com glaucoma de tensao normal (GTN)", *Rev Bras Oftal*, vol. 58 pp. 459–462, 1999, Abstract.

Bosworth, C.F. et al "Spatial relationship of motion automated perimetry and optic disc topography in patients with glaucomatous optic neuropathy",*J Glaucoma*, vol. 8, pp. 281–289, 1999, Abstract.

Bowd, C. et al. "Optic disk topography after medical treatment to reduce intraocular pressure",*Am J Ophthalmol*, vol. 130 pp. 280–286, 2000, Abstract.

Bowd, C. et al. "Imaging of the optic disc and retinal nerve fiber layer: the effects of age, optic disc area, refractive error, and gender", *J Opt Soc Am A*, vo.19 pp. 197–207, 2002, Abstract.

Bowd, C. et al. "Comparing neural networks and linear discriminant functions for glaucoma detection using confocal scanning laser ophthalmology of the optic disc", *Invest Ophthalmol Vis Sci*, vol. 43 pp. 3444–3454, 2002, Abstract.

Breil, P. et al. "[An intraindividaul comparison of the relationship between blood flow velocities in retrobulbar vessels and glaucomatous damage.] Verhältnis zwischer retrobulbären Blutflussgeschwindigkeiten and glaukomatösem Schaden. Ein intraindividueller Vergleich.", *Opthalmologe*, vol. 99 pp. 613–616, 2002, Abstract.

Brigatti, L. et al. "Correlation of visual field with scanning confocal laser optic disc measurements in glaucoma. [published erratum appears in Arch Ophthalmol 1996;114:424]", *Arch Opthalmol*, vol. 113 pp. 1191–1194, 1995, Abstract.

Brigatti, L. et al. "Regional test–retest variability of confocal scanning laser tomography", *Am J Ophthalmol*, vol. 120 pp. 433–440, 1995, Abstract.

Broadway, D.C. et al. "The ability of scanning laser opthalmoscopy to identify various glaucomatous optic disc appearances", *Am J Ophthalmol*, vol. 125 pp. 593–604, 1998, Abstract.

Budde, W.M. et al. "Chalcosis Oculi", *Klin Monatsbl Augenheilkd*, vol. 212 pp. 184–185, 1998, Abstract.

Budde, W.M. et al. "Determination of optic cup depth by confocal scanning laser tomography", *Eur J Ophthalmol*, vol. 12, pp. 42–48, 2003, Abstract.

Burk, R.O.W. "[3–Dimensional topographic analysis of the papilla as a component of glaucoma diagnosis.] Die dreidimensionale topographische Analyse der Papille als Bestandteil der Glaukomidiagnostik", *Opthalmologe*, vol. 89 pp. 190–203, 1992, Abstract.

Burk, R.O.W. et al. "Current imaging of the optic disk and retinal nerve fiber layer", *Curr Opin Ophthalmol*, vol. 7 pp 99–108, 1996, Abstract.

Burk, R.O.W. et al. "Laser scanning tomography of localised nerve fibre layer defects", *Br J Ophthalmol*, vol. 82 pp. 1112–1117, 1998, Abstract.

Burk, R.O.W. et al. "Development of the standard reference plane for the Heidelberg Retina Tomograph", *Graefas Arch Clin Exp Ophthalmol*, vol. 238 pp. 375–384, 2000, Abstract.

Burk, R.O.W. "[Laser Scanning Tomography: Interpretation of the HRTII printout.] Laser Scanning Topograpie: Interpretatin der Austrucke des Heidelberg Retina Tomographen HRTII.", *Z prakt Augenheilkd*, vol. 22 pp. 183–190, 2001, Abstract.

Burk, R.O.W. et al. "Clinical detection of optic nerve damage. Measuring changes in cup steepness with use of a new image alignment algorithm", *Surv Ophthalmol*, vol. 45 pp. S297–S303, 2001, Abstract.

Caprioli, J. et al. "Slope of the peripapillary nerve fibre later surface in glaucoma", *Invest Ophthalmol Vis Sci*, vol. 39 pp. 2321–2328, 1998, Abstract.

Chauhan, B.C. et al. "Test–retest variability of topographic measurements with confocal scanning laser tomography in patients with glaucoma and control subjects", Am J Ophthalmol, vol. 118 pp. 9–15, 1994, Abstract.

Chauhan, B.C, et al. "Effect of the cardiac cycle on topographic measurements using confocal scanning laser tomography", *Graefas Arch Clin Exp Ophthalmol*, vol. 233 pp. 568–572, 1995, Abstract.

Chauhan, B.C. et al. "Influence of time separation on variability estimates of topographic measurements with confocal scanning laser tomography", *J Glaucoma*, vol. 4 pp. 189–193, 1995, Abstract.

Chauhan, B.C. et al. "Technique for detecting serial topographic changes in the optic disc and peripapillary retina using scanning laser tomography", *Invest Ophthalmol Vis Sci*, vol. 41 pp. 775–782, 2000, Abstract.

Chauhan, B.C. et al. "Optic disc and visual field changes in a prospective longitudinal study of patients with glaucoma. Comparison of scanning laser tomography with conventional perimetry and optic disc photography", *Arch Ophthalmol*, vol. 119 pp. 1492–1499, 2001, Abstract.

Chauhan, B.C. et al. "Effect of intraocular pressure on optic disc topography, electroretinography, and axonal loss in a chronic pressure–induced rat model of optic nerve damage", *Invest Ophthalmol Vis Sci*, vol. 43 pp. 2969–2976, 2002, Abstract.

Chen, E. et al., "Thinning of the papillomacular bundle in the glaucomatous eye and its influence on the reference plane of the Heidelberg Retinal Tomography", *J Glaucoma*, vol. 10 pp. 386–399, 2001, Abstract.

Darchuk, V. et al. "Optic nerve head behavior in Posner–Schlossman syndrome", *Int. Ophthalmol*, vol. 23 pp. 373–379, 2001, Abstract.

Dichtl, A. et al. "Comparison between tomographic scanning evaluation and photographic measurement of the neuroretinal rim", *Am J Ophthalmol*, vol. 121 pp. 494–501, 1996, Abstract.

Drexler, W. et al. "Dual–beam optical coherence tomography and topography of the human eye: A clinical feasibility study", *Proc. SPIE*, vol. 2930, *Lasers in Opthalmology IV*, pp. 183–193, 1996.

Eid, T.M. et al. "Quantitative estimation of retinal nerve fiber layer height in glaucoma and the relationship with optic nerve head topography and visual field", *J Glaucoma*, vol. 6, pp. 221–230, 1997, Abstract.

Eid, T.E. et al. "Quantitative differences between the optic nerve head and peripapillary retina in low–tension and high–tension primary open–angle glaucoma", *Am J Ophthalmol*, vol. 124 pp. 805–813, 1997, Abstract.

Emdadi, A. et al. "Patterns of optic disk damage in patients with early focal visual field loss", *Am J Ophthalmol*, vol. 126 pp. 763–771, 1998, Abstract.

Emdadi, A. et al. "Parapapillary atrophy in patients with focal visual field loss", *Am J Ophthalmol*, vol. 128 pp. 595–600, 1999, Abstract.

Ford, B.A. et al. "Comparison of data analysis tools for detection of glaucoma with the Heidelberg Retina Tomograph", *Ophthalmology*, vol. 110 pp. 1145–1150, 2003, Abstract.

Freeman, W.R. "New ophthalmic lasers for evaluation and treatment of retinal disease", *Australian New Zealand J Ophthalmol*, vol. 21, pp. 139–146, 1993, Abstract.

Funk, J. "Imaging of the optic disc in glaucoma: Which way to go?", *Curr. Opin Ophthalmol*, vol. 9 pp. 71–76, 1998, Abstract.

Garway–Heath, D.F. et al. "Aging changes of the optic nerve head in relation to open angle glaucoma", *Br J Ophthalmol*, vol. 81 pp. 840–845, 1997, Abstract.

Garway–Health, D.F. et al. "Measurement of optic disc size: Equivalence of methods to correct for ocular magnification", *Br J Ophthalmol*, vo. 82 pp. 643–649, 1998, Abstract.

Garway–Heath, D.F. et al. "Inter–and intraobserver variation in the analysis of optic disc images:Comparison of the Heidelberg Retina Tomograph and computer assisted planimetry", *Br J Ophthalmol*, vol. 83 pp. 664–669, 1999.

Garway–Heath, D.F. et al. "Relationship between Electrophysiological, Psychophysical, and Anatomical Measurements of Glaucoma", *Invest Ophthalmol Vis Sci*, vol. 43 pp. 2213–2220, 2002, Abstract.

Gherghel, D. et al. "Interocular differences in optic disc topographic parameters in normal subjects", *Curr Eye Res*, vol. 20 pp. 276–282, 2000, Abstract.

Girkin, C.A. et al. "Racial differences in the association between optic disc topography and early glaucoma", *Invest Ophthalmol Vis Sci*, vol. 44 pp. 3382–3387, 2003, Abstract.

Göbel, W. et al. "[Quantitative and objective follow–up of papilledema with the Heidelberg Retina Tomograph.] Quantitative und objective Verlaufskontrolle der Papillenschwellung mit dem Heidelberg Retina Tomographen", *Ophthalmologe*, vol. 94 pp. 673–677, 1997, Abstract.

Gordon, M.O. et al. "The Ocular Hypertensive Treatment Study", *Arch Ophthalmol*, vol. 117 pp. 573–583, 1999, Abstract.

Gramer, E. et al. "Measurement of the retinal nerve fiber layer thickness in clinical routine", *Curr Opin Ophthalmol*, vol. 9 pp. 77–87, 1998, Abstract.

Greaney, M.J. et al. "Comparison of optic nerve imaging methods to distinguish normal eyes from those with glaucoma", *Invest Ophthalmol Vis Sci*, vol. 43 pp. 140–145, 2002, Abstract.

Gugleta, K. et al. "Asymmetry in intraocular pressure and retinal nerve fiber layer thickness in normal–tension glaucoma", *Ophthalmologica*, vol. 213 pp. 219–223, 1999, Abstract.

Gulati, V. et al. "Correlation analysis of visual field thresholds and scanning laser ophthalmoscopic optic nerve head measurements in glaucoma", *Ophthalmic Physiol Opt*, vol. 23 pp. 233–242, 2003, Abstract.

Gundersen, K.G. et al. "Age, gender, IOP, and refraction and optic disc topography in normal eyes. A cross–sectional study using raster and scanning laser tomography", *Acta Ophthalmol Scand*, vol. 76 pp. 170–175, 1998, Abstract.

Gundersen, K.G. et al. "Comparability of three–dimensional optic disc imaging with different techniques. A study with confocal scanning laser tomography and raster tomography", Acta Ophthalmol Scand, vol. 78 pp. 9–13, 2000, Abstract.

Gundersen, K.G. et al. "Comparison of ranked segment analysis (RSA) and cup to disc ration in computer assisted optic disc evaluation", *Acta Ophthalmol Scand*, vol. 78 pp. 137–141, 2000, Abstract.

Gurses–Ozden, R. et al. "Retinal nerve fiber layer thickness remains unchanged following laser–assisted in situ keratomileusis", *Am J Ophthalmol*, vol. 132 pp. 512–516, 2001, Abstract.

Harju, M. et al. "Scanning laser ophthalmoscopy of the optic nerve head in exfoliation glaucoma and ocular hypertension with exfoliation syndrome", *Br J Ophthalmol*, vol. 85 pp. 297–303, 2001, Abstract.

Harris, A. et al. "Blood lfow per unit retinal nerve fibre tissue volume is lower in the human inferior retina", *Br J Ophthalmol*, vol. 87 pp. 184–188, 2003, Abstract.

Hatch, W.V. et al. "Laser'scanning tomography of the optic nerve head in ocular hypertension and glaucoma", *Br J Ophthalmol*, vol. 81 pp. 871–876, 1997, Abstract.

Hatch, W.V. et al. "Agreement in assessing glaucomatous discs in a clinical teaching setting with stereoscopic disc photographs, planimetry, and laser scanning tomography", *J Glaucoma*, vol. 8 pp. 99–104, 1999, Abstract.

Hatch, W.V. et al. "Interobserver agreement of Heidelberg Retina Tomography parameters", *J Glaucoma*, vol. 8 pp 232–237, 1999, Abstract.

Hosking, S.L. et al. "Prospective study design for the Heidelberg Retina Tomograph: The effect of change in focus setting", *Graefes Arch Clin Exp Ophthalmol*, vol. 234 pp. 306–310, 1996, Abstract.

Hosking, S.L. "An A B C of glaucoma: Apoptosis, blood flow and confocal imaging," *Ophthalmic Physiol Opt*, vol. 18 pp. 133–139, 1998, Abstract.

Hosking, S. et al. "Scanning laser tomography: Effect of change in keratomoetry values on retinal distance measures", *Ophthalmic Physiol Opt*, vol. 18 pp. 294–298, 1998, Abstract.

Hudson, C. et al. "Objective morphological assessment of macular hole surgery by scanning laser tomography", *Br J Ophthalmol*, vol. 81 107–116, 1997, Abstract.

Hudson, C. et al. "Scanning laser tomography z profile signal width as an objective index of macular retinal thickening", *Br J Ophthalmol*, vol. 82 pp. 121–130, 1998, Abstract.

Hudson, C. et al. "Correlation of a scanning laser derived oedema index and visual function following grid laser treatment for diabetic macular oedema", *Br J. Ophthalmol*, vol. 87 pp. 455–461, 2003, Abstract.

Hutchings, N. et al. "Long–term fluctuation in short–wavelength automated perimetry in glaucoma suspects and glaucoma patients", *Invest Ophthalmol Vis Sci*, vol. 42 pp. 2332–2337, 2001, Abstract.

Ieong, A. et al. "Sensitivity and specificity of two glaucoma case–finding strategies for optometrists", *Ophthalmic Physiol Opt*, vol. 23 pp. 341–346, 2003, Abstract.

Iester, M. et al. "Correlation between the visual field indices and Heidelberg Retina Tomography parameters", *J Glaucoma*, vol. 6 pp. 78–82, 1997, Abstract.

Iester, M. et al. "The effect of optic disc size on diagnostic precision with the Heidelberg Retina Tomograph", *Ophthalmology*, vol. 104, pp. 545–548, 1997, Abstract.

Iester, M. et al. "A comparison of health, ocular hypertensive, and glaucomatous optic disc topographic parameters", *J Glaucoma*, vol. 6 pp. 363–370, 1997, Abstract.

Iester, M. et al. "Sector–based analysis of optic nerve head shape parameters and visual field indices in healthy and glaucomatous eyes",*J Glaucoma*, vol. 6 pp. 371–376, 1997, Abstract.

Iester, M. et al. "ROC analysis of Heidelberg Retina Tomograph optic disc shape measures in glaucoma", *Can J Ophthalmol*, vol. 32 pp. 382–388, 1997, Abstract.

Iester, M. et al. "Retinal nerve fiber layer height in the high–tension glaucoma and healthy eyes", *J Glaucoma*, vol. 7 pp. 1–7, 1998, Abstract.

Iester, M. et al. "Optic nerve head morphologic characteristics in high–tension and normal–tension glaucoma", *Arch Ophthalmol*, vol. 117 pp. 1010–1013, 1999, Abstract.

Iester, M. t al. "Topographic analysis to discriminate glaucomatous from normal optic nerve heads with a confocal scanning laser: New optic disk analysis without any observer input", *Surv Ophthalmol*, vol. 44 Suppl.1 pp. S33–40, 1999, Abstract.

Iester, M. et al. "Discriminant analysis models for early detection of glaucomatous optic disc changes", *Br J Ophthalmol*, vol. 84 pp. 464–468, 2000, Abstract.

Iester, M. et al. "Retinal nerve fiber layer and physiological central corneal thickness", *J Glaucoma*, vol. 10 pp. 158–162, 2001, Abstract.

Iester, M. et al. "Interobserver variability of optic disk variables measured by confocal scanning laser tomography", *Am J Ophthalmol*, vol. 132 pp. 57–62, 2001, Abstract.

Iester, M. et al. "Discriminant analysis formulas of optic nerve head parameters measured by confocal scanning laser tomography", *J Glaucoma*, vol. 11 pp. 97–104, 2002, Abstract.

Ikran, M.K. et al. "Comparing ophthalmoscopy, slide viewing, and semiautomated systems in optic disc morphometry", *Ophthalmology*, vol. 109 pp. 486–493, 2002, Abstract.

Irak, I et al. "Change in optic disk topography alter trabeculectomy", *Am J Ophthalmol*, vol. 122 pp. 690–695, 1996, Abstract.

Itai, N. et al. "Comparison of optic disk topography measured by Retinal Thickness Analyzer with measurement by Heidelberg Retina Tomograph II", *Jpn J Ophthalmol*, vol. 47 pp. 214–220, 2003, Abstract.

Jaakkola, A. et al. "The use of confocal scanning laser tomography in the evaluation of retinal elevation in age related macular degeneration", *Ophthalmology*, vol. 106 pp. 274–279, 1999, Abstract.

Janknecht, P. et al. "[The Heidelberg Retina Tomograph: Reproducibility and measuring errors in different papillary widths using a model eye.] Heidelberg Retina Tomograph: Reproduzierbarkeit und Meβfehler bei unterschiedlicher Pupillenweite am Modellauge", *Klin Monatsbl Augenheilkd*, vol. 205, pp. 98–102, 1994, Abstract.

Janknecht, P. et al. "Optic nerve head analyzer and Heidelberg Retina Tomograph: Accuracy of topographic measurements in a model eye and in volunteers", *Br J Ophthalmol*, vol. 78 pp. 760–768, 1994, Abstract.

Janknecht, P. et al. "Optic nerve head analyzer and Heidelberg Retina Tomograph: Relative error and reproducibility of topographic measurements in a model eye with simulated cataracts", *Graefes Arch Clin Exp Ophthalmol*, vol. 233 pp. 523–529, 1995, Abstract.

Janknecht, P. et al. "[Reproducibility of measurements with the Heidelberg retina tomography in fundus elevations.] Reproduzierbarkeit von Messungen mit dem Heidelberg Retina Tomographen bie Fundusprominenzen", *Opthalmologe*, vol. 92 pp. 862–865, 1995, Abstract.

Janknecht, P. "[Spontaneous resolution of a macular pucker.] Spontane Ablösung eines Macular Puckers", *Klin Monatsbl Augenheilkd*, vol. 211 pp. 398–399, 1997, Abstract.

Jonas, J.B. et al. "Comparison of measurements of neuroretinal rim area between comnfocal laser scanning tomography and planimetry of photographs", Br J Ophthalmol, vol. 82 pp. 363–366, 1998, Abstract.

Joos, K.M. et al. "Measurement of retinal vessel diameters in imaged Produced by the Heidelberg Retinal Tomograph", Proc SPIE vol. 2971, Ophthalmic Technologies VII, Washington, pp. 35–39, 1997.

Joos, K.M. et al. "Modification of the Heidelberg retinal laser tomography and flowmeter to allow measurements in supine patients", Proc SPIE vol. 3246, Ophthalmic Technologies VII, pp. 61–64, 1998.

Kalaboukhova, L. et al. "Frequency doubling technology and high–pass resolution perimetry in glaucoma and ocular hypertension", *Acta Ophthalmol Scand*, vol. 81 pp. 247–252, 2003, Abstract.

Kamal, D.S. et al. "Detection of optic disc change with the Heidelberg Retina Tomograph before confirmed visual field change in ocular hypertensives converting to early glaucoma", *Br J Ophthalmol*, vol. 83 pp. 290–294, 1999, Abstract.

Kamal, D.S. et al. "Use of sequential Heidelberg retina tomography images to identify changes at the optic disc in ocular hypertensive patients at risk of developing glaucoma", *Br J Ophthalmol*, vol. 84 pp. 993–998, 2000, Abstract.

Kamal, D. et al. "Results of the betaxolol versus placebo treatment trial in ocular hypertension", *Graefe's Arch Clin Exp Ophthalmol*, vol. 241 pp. 196–203, 2003, Abstract.

Kergoat, H. et al. "Age–related topographical changes in the normal human optic nerve head measured by scanning laser tomography", *Optom Vis Sci*, vol. 78 pp. 431–435, 2001, Abstract.

Kergoat, H. et al. "Normal Optic nerve head topography in the early stages of dementia of the Alzheimer type", *Dement Geriatr Cogn Disord*, vol. 12 pp. 359–363, 2001, Abstract.

Kesen, M.R. et al. "The Heidelberg Retina Tomograph vs clinical impression in the diagnosis of glaucoma", *Am J Ophthalmol*, vol. 133 pp. 613–616, 2002, Abstract.

Kim, T.W. "Neuroprotective effect of memantine in a rabbit model of optic nerve ischemia", *Korean J Ophthalmol*, vol. 16 pp. 1–7, 2002, Abstract.

King, A.J.W. "Measurement of peripapillary retinal nerve fiber layer volume in glaucoma", *Am J Ophthalmol*, vol. 129 pp. 599–607, 2000, Abstract.

Klemm, M. et al. "[Quantification of the thickness of the retinal nerve fibre layer. A comparison of laser scanning ophthalmology, polarimetry and optical coherence tomography of eyes from health patiens and patients with primary open angle glaucoma.] Quatifizierung der retinalen Nervenfaserschichtdicke. Ein Vergleich von Laser–Scanning–Ophthalmoskopie, Polarimetrie und Optischer Kohärenztomographie bei gesunden und glaukomkranken Augen", *Ophthalmologe*, vol. 98 pp. 832–843, 2001, Abstract.

Klemm, M. et al. "[Reproducibility of measurements of the retinal nerve fibre layer thickness. Comparison of OCT with NFA and HRT.]", *Ophthalmologe*, vol. 99 345–351, 2002, Abstract.

Kobayashi, H. et al. "Correlation of quantitative three–dimensional measurements of macular hole size with visual acuity after virectomy", Graefes Arch Clin Exp Ophthalmol, vol. 237 pp. 283–288, 1999, Abstract.

Kobayashi, H. et al. "Quantitative measurements of changes of idiopathic stage 3 macular holes after riectomy using confocal scanning laser tomography", *Graefes Arch Clin Exp Ophthalmol*, vol. 238 pp. 410–419, 2000, Abstract.

Kobayashi, H. et al. "Macualr hole and myopic refraction", *Br J Ophthalmol*, vol. 86 pp. 1269–1273, 2002, Abstract.

Konno, S. et al. "Three–dimensional analysis of macular diseases with a scanning retinal thickness analyzer and a confocal scanning laser opthalmoscope", Ophthalmic Surg Lasers, vol. 323, pp. 95–99, 2001, Abstract.

Kono, Y. et al. "["Neural capacity" index correlates with neuroretinal rim area of glaucomatous eyes better than light sensitivity]", *Nippon Ganka Gakkai Zasshi*, vol. 100 p. 223–229, 1996, Abstract.

Kono, Y. et al. "High–pass resolution of perimetry and a Humphrey field analyzer as indicators of glaucomatous optic disc abnormalities", *Ophthalmology*, vol. 104 pp. 1496–1502, 1997, Abstract.

Kono, Y. et al. "Agreement of measurement of parapapillary atrophy with confocal laser opthalmoscopy and planimetry of photographs", *J Glaucoma,* vol. 8 pp. 105–110, 1999, Abstract.

Kono, Y. et al. "Relationship between parapapillary atrophy and visual field abnormality in primary open–angle glaucoma", *Am J Ophthalmol,* vol. 127 pp. 674–680, 1999, Abstract.

Kotecha, A. "Optic disc changes following trabeculectomy: Longitudinal and localization of change", *Br J Ophthalmol,* vol. 85 pp. 956–961, 2001, Abstract.

Krzyzanowska, P. et al. "[The comparative analysis of changes in optic disc morphology after trabeculectomy, measured by scanning laser tomography.]", Klin Oczna, vol. 104 pp. 122–127, 2002, Abstract.

Kuchenbecker, J. et al. "[Quantitative and objective topometrical analysis of drusen of the optic nerve head with the Heidelberg retina tomography (HRT).] Quantitative und objective topo–metrische Analyse von Drusenpapillen mit dem Heidelberg–Retina–Tomographen (HRT)", Opthalmologe, vol. 99 pp. 768–773, 2002, Abstract.

Lee, B.L. et al. "Change in optic disc topography associated with diurnal variation in intraocular pressure", J Glaucoma, vol. 8 pp. 221–223, 1999, Abstract.

Lee, K.H. et al. "Relationship between optic nerve head parameters of Heidelberg Retina Tomograph and visual field defects in primary open–angle glaucoma", *Korean J Ophthalmol,* vol. 10 pp. 24–28, 1996, Abstract.

Lesk, M.R. et al. "Reversal of optic disc cupping after glaucoma surgery analyzed with a scanning laser tomograph", *Opthalmology,* vol. 106 pp. 1013–1018, 1999, Abstract.

Lim, C.S. et al. "A simple clinical method to measure the optic disc size in glaucoma", *J Glaucoma,* vol. 5 pp. 241–245, 1996, Abstract.

Liou, S. et al. "Morphometric characteristics of optic disk with disk hemorrhage in normal–tension glaucoma", *Am J Ophthalmol,* vol. 132, pp 618–625, 2001, Abstract.

Liu, X. et al. "Study on stereometric parameters of optic nerve head of normal, big–cupped disk and glaucomatous eyes using Heidelberg retina tomograph", *Yan Ke Xue Bao,* vol. 16 pp. 163–167, 2000, Abstract.

Lusky, M. et al. "Effects of intraocular pressure reduction on optic nerve head topography", *Curr Opin Ophthalmol,* vol. 4 pp. 40–43, 1993, Abstract.

Lusky, M. et al. "Reproducibility of optic nerve head topography measurements in eyes with undilated pupils", *J Glaucoma,* vol. 2 pp. 104–109, 1993, Abstract.

Maier, H. et al. [Sensitivity and specificity of the Heidelberg retinal tomography for imaging nerve fiber bundle defects in glaucoma patients with localized visual field defects.] Sensitivatät und Spezifizität des Heidelberg Retina Tomagraphen für die Darstellung von Nervenfaserbündeldefekten bei Glaukompatienten mit lokalisierten Gesichtsfeldausfällen, Opthalmologe, vol. 92, pp. 521–525, 1995, Abstract.

Malinosvky, V.E. "An overview of the Heidelberg Retina Tomograph", *J Am Optom Assoc,* vol. 67, pp. 457–467, 1996, Abstract.

Mansberger, S.L. et al. "Achromatic and short–wavelength automated perimetry in patents with glaucomatous large cups", *Arch Ophthalmol,* vol. 117 pp. 1473–1477, 1999, Abstract.

Mardin, C.Y. et al. "[Are there genuine and pseudo–normal pressure glaucoma? Body position–dependent intraocular pressure values in normal pressure glaucoma.] Gibt es echte und Pseudonormal druckglaukome? Lageabhängiges Druckverhalten bei Normaldruckglaukom", *Klin Monasbl Augenheilkd,* vol. 211 pp. 235–240, 1997, Abstract.

Mardin, C.Y. et al. "Influence of optic disc size on the sensitivity of the Heidelberg Retina Tomograph", *Graefes Arch Clin Exp Ophthalmol* , vol. 236 pp. 641–645, 1998, Abstract.

Mardin, C.Y. et al. "Preperimetric glaucoma diagnosis by confocal scanning laser tomography of the optic disc", *Br J Ophthalmol,* vol. 83 pp. 299–304, 1999, Abstract.

Mardin, C.Y. et al. "Quantification of aqueous melanin granules, intraocular pressure and glaucomatous damage in primary pigment dispersion syndrome", Ophthalmology, vol. 107 pp. 435–440, 2000, Abstract.

Mardin, C.Y. et al. "Morphometrische Querschnittsverlaufsbeobachtung der Papille mit dem HRT in Augen mit morphologischer Progression der glaukomatösen Atrophie der Papilla des Nervus opticus", *Klin Monatsbl Aguenheilkd,* vol. 217 pp. 82–87, 2000, Abstract.

Mardin, C.Y. et al. "The diagnostic value of optic nerve imaging in early glaucoma", *Curr Opin Ophthalmol,* vol. 12 pp. 100–104, 2001, Abstract.

Marengo, J. et al. "Glaucomatous optic nerve head changes with scanning laser ophthalmoscopy", *Int. Ophthalmol,* vol. 23 pp. 413–423, 2001, Abstract.

Martin, L.M. "Concordance between results of optic disc tomography and high–pass resolution perimetry in glaucoma", *J Glaucoma,* vol. 9 pp. 28–33, 2000, Abstract.

Mashima, Y. et al. "Optic disc excavation in the atrophic stage of Leber's hereditary optic neuropathy: comparison with normal tension glaucoma", Graefe's Arch Clin Exp Ophthalmol, vol. 241 pp. 75–80, 2003, Abstract.

Menezes, A.V. et al. "Reproducibility of topographic measurements of the macula with a scanning laser ophthalmoscope", *Ophthalmology,* vol. 102 pp. 230–235, 1995, Abstract.

Meyer, J.H. et al. "Blind spot size depends on the optic disc topography: A study using SLO controlled scotometry and the Heidelberg Retina Tomograph", Br J Ophthalmol, vol. 81 pp. 355–359, 1997, Abstract.

Meyer, J.H. et al. "[Does the fundus perimetry determined edge of the blind spot depend on the superficial form of the papilla?]", Ophthalmologe, vol. 94 pp. 360–363, 1997, Abstract.

Meyer, J.H. et al. "Is the blind spot enlarged in early glaucoma?", *Eur J Ophthalmol,* vol. 8 pp. 28–32, Abstract.

Meyer, T. et al. "How large is the optic disc? Systematic errors in fundus cameras and topographers", *Ophthalmic Physiol Opt,* vol. 21 pp. 139–150, 2001, Abstract.

Michelson, G. et al. "Screening models for glaucoma", *Curr Opin Ophthalmol,* vol. 12 pp. 105–111, 2001, Abstract.

Miglior, S. et al. "Clinical ability of Heidelberg retinal tomography examination to detect glaucomatous visual field changes", *Opthalmology,* vol. 108 pp. 1621–1627, 2001, Abstract.

Miglior, S. et al. "Intraobserver and interobserver reproducibility in the evaluation of optic disc stereometric parameters by Heidelberg Retina Tomograph", Ophthalmology, vol. 109 pp. 1072–1077, 2002, Abstract.

Miglior, S. et al. "Detection of glaucomatous visual field changes using the Moorfields regression analysis of the Heidelberg retina tomograph", *Am J Ophthalmol*, vol. 136 pp. 26–33, 2003, Abstract.

Mikelberg, F.S. et al. "Reproducibility of topographic parameters obtained with the Heidelberg Retina Tomograph", *J Glaucoma*, vol. 2 pp. 101–103, 1993, Abstract.

Mikelberg, F.S. et al. "Ability of the Heidelberg Retina Tomograph to detect early glaucomatous visual field loss", *J Glaucoma*, vol. 4 pp. 242–247, 1995, Abstract.

Mistlberger, A. et al. "Heidelberger Retina Tomography and optical coherence tomography in normal, ocular–hypertensive, and glaucomatous eyes", Ophthalmology, vol. 106 pp. 2027–2032, 1999, Abstract.

Miyake, K. et al. "Quantification of retinal nerve fiber defects in Glaucoma: three–dimensional analysis by Heidelberg retina tomograph", Jpn J Ophthalmol, vol. 47 pp. 347–350, 2003, Abstract.

Mojon D.S., "[Examination of the optic disc and nerve fiber layer in glaucoma] Untersuchung der Papille und Nervenfaserschicht beim Glaukom", Klin Monatsbl Augenheilkd vol. 214 pp. 295–299, 1999, Abstract.

Morgan, W.H. et al., "Optic Disc Movement with Variations in Intraocular and Cerebrospinal Fluid Pressure", Invest Ophthalmol Vis Sci, vol. 43 pp. 3236–3242, 2002, Abstract.

Morgan–Davies J. et al., "Measurement of a novel optic disc topographic parameter, 'spikiness', in glaucoma" Graefes Arch Clin Exp Ophthalmol, vol. 238 pp. 669–676, 2000, Abstract.

Moussalli, M.A. et al., "Arterial narrowing as a predictive factor in glaucoma" Int Ophthalmol, vol. 23 pp. 271–274, 2001, Abstract.

Moussalli, M.A. et al. "Papillary drusen and ocular hypertension" *Int Ophthalmol*, vol. 23 pp 275–278, 2001, Abstract.

Mulholland, D.A. et al., "Use of scanning laser ophthalmoscopy to monitor papilloedema in idiopathic intracranial hypertension" *Br J Ophthalmol*, vol 82 pp 1301–1305, 1998, Abstract.

Muller–Richter, U.D.A. et al., [Preliminary clinical experience with the Dresdner 3D display as add–on to the Heidelberg Retina Tomograph (HRT)] Erste klinische Erfahrungen mit dem Dresdner 3D–Display als Zusatz zum Heidelberg Retina Tomographen (HRT) *Klin Monatsbl Augenheilkd*, vol. 215 pp. 182–185, 1999, Abstract.

Muller–Richter, U.D. et al. "Three–dimensional analysis of measurements of the Heidelberg Retina Tomograph" *Graefes Arch Clin Exp Ophthalmol*, vol. 238 pp. 746–751, 2000, Abstract.

Muller–Richter, U.D. et al. "[Better assessment of HRT measurements by three–dimensional presentation] Bessere Auswertung von HRT–Aufnahmen durch dreidimensionale Darstellung" *Ophthalmologe*, vol. 98 pp. 859–863, 2001, Abstract.

Nakamura, H. et al. "[Use of a scanning laser tomograph to evaluate the optic disc of the normal eyes]" *Nippon Ganka Gakkai Zasshi*, vol. 102 pp. 378–382, 1998, Abstract.

Nakamura, H. et al. "Scanning laser tomography to evaluate optic discs of normal eyes" *Jpn J Ophthalmol*, vol. 43 pp. 410–414, 1999, Abstract.

Nyman, K. et al. "Correlation of asymmetry of visual field loss with optic disc topography in normal–tension glaucoma" *Arch Ophthalmol*, vol. 112 pp. 349–353, 1994, Abstract.

Orgul, S. et al. "Reproducibility of topometric data with a scanning laser ophthalmoscope in rabbits" *Jpn J Ophthalml*, vol. 39 pp. 438–442, 1995, Abstract.

Orgul, S. et al. "Sources of variability of topometric data with a scanning laser ophthalmoscope" *Arch Ophthalmol*, vol. 114 p. 161–164, 1996, Abstract.

Orgul, S. et al. "An endothelin–1 induced model of optic nerve ischemia in the rabbit" *Invest Ophthalmol Vis Sci*, vol. 37 pp. 186–1869, 1996, Abstract.

Orgul, S. et al. "Variability of contour line alignment on sequential images with the Heidelberg Retina Tomograph", *Graefes Arch Clin Exp Ophthalmol*, vol. 235 pp. 82–86, 1997, Abstract.

Park, H.J. "Circumferential profiles of peripapillary surface height with confocal scanning laser ophthalmoscopy" *Korean J Ophthalmol*, vol. 11 pp. 7–14, 1997, Abstract.

Park, K.H. et al. "Correlation between peripapillary atrophy and optic nerve damage in normal–tension glaucoma" *Ophthalmology*, vol. 103 pp. 1899–1906, Abstract.

Park, K.H. et al. "Short–term change of optic nerve head topography after trabeculectomy in adult glaucoma patients as measured by Heidelberg Retina Tomograph" *Korean J Ophthalmol*, vol. vol. pp. 1–6, 1997, Abstract.

Park, K.H. et al. "Reversal of optic disc togography in patients with glaucomatocyclitic crisis after remission of attack" *J Glaucoma*, vol. 7 pp. 225–229, 1998, Abstract.

Park, K.H. et al. "Ability of peripapillary atrophy parameters to differentiate normaltension glaucoma from glaucomalike disk" *J Glaucoma*, vol. 10 pp. 95–101, 2001 Abstract.

Park, K.H. et al "Development of a novel reference plane for the Heidelberg Retina Tomograph with optical coherence tomography measurements" *J Glaucoma*, vol. 11 pp. 385–391, 2002, Abstract.

Pauleikhoff, D. et al. "Pigment epithelial detachment in the elderly. Clinical differentiation, natural course and pathogenetic implications" *Graefe's Arch Clin Exp Ophthalmol*, vol. 240. pp. 533–538, 2002, Abstract.

Piette, S. "Acute conformational changes in the optic nerve head with rapid intraocular pressure elevation: implications for LASIk Surgery" *Ophthalmic Surg Lasers Imaging*, vol. 34 pp. 334–341, 2003, Abstract.

Plummer, D.J. et al. "Retinal nerve fiber layer evaluation in human immunodeficiency virus–positive patients" *Am J Ophthalmol*, vol. 1 131 pp. 216–222, 2001, Abstract.

Raitta, C. et al. "Optic disc topography before and after trabeculectomy in advance glaucoma" *Ophthalmic Surg Lasers*, vol. 27 pp. 349–354, 1996, Abstract.

Rakebrandt, F. et al. "The construction of a model eye for the investigation of laser–tissue interactions in scanning laser ophthalmoscopy" Optom Vis Sci, vol. 80 pp. 252–258, 2003, Abstract.

Roff, E.J. et al. "The influence of contour line size and location on the reproducibility of topographic measurement with the Heidelberg Retina Tomograph" *Ophthalmic Physiol*, vol. 21 pp. 173–181, 2001, Abstract.

Rohrschneider, K. et al. "Comparison of two laser scanning tomography systems for three–dimensional analysis of the optic papilla" *Ophthalmologe*, vol. 90 pp. 613–619, 1993, Abstract.

Rohrschneider, K. et al. "Reproducibility of optic nerve head topography with a new laser tomographic scanning device" *Ophthalmology*, vol. 101, pp. 1 1044–1049, 1994, Abstract.

Rudnicka, A.R. et al. "Magnification characteristics of fundus imaging systems" *Ophthalmology,* vol. 105, pp. 2186–2192, 1998, Abstract.

Salgarello, T. et al. "Correlation of pattern electroretinogram with optic disc cup shape in ocular hypertension" *Invest Ophthalmol Vis Sci,* vol. 40, pp. 1989–1997, 1999, Abstract.

Salgarello, T. et al. "Correlation of optic nerve head tomography with visual field sensitivity in papilledema" *Invest Ophthalmol Vis Sci,* vol. 42, pp. 1487–1494, 2001, Abstract.

Sampaolesi, R. et al. "Laser scanning tomography of the optic disk with the Heidelbert Retina Tomograph (HRT) in congenital glaucoma and goniodysgenesis" Krieglstein GK (ed) *Glaucoma Update V,* Kaden Verlag, pp. 158–167, 1996.

Sampaolesi, R. et al. "The pseudoglaucomas" *Int Ophthalmol,* vol. 23, pp. 267–269, 2001, Abstract.

Sampaolesi, R., et al. "Large Optic nerve heads: megalopapilla or megalodics" *Int Ophthalmol,* vol. 23, pp. 251–257, 2001, Abstract.

Sampaolesi, R. et al. "Optic nerve head damage progression in patients with glaucoma" *Int Ophthalmol,* vol. 23 pp. 259–261, 2001, Abstract.

Sampaolesi, R. et al. "Congenital anomalies of the optic nerve head–review" *Int Ophthalmol,* vol. 23, pp. 263–265, 2001, Abstract.

Sanchez–Galeana, C. et al. "Using optical imaging summary data to detect glaucoma" *Ophthalmology,* vol. 108, pp. 1812–1818, 2001, Abstract.

Saruhan, A. et al. "Descriptive information of topographic parameters computed at the optic nerve head with the Heidelberg Retina Tomograph" *J Glaucoma,* vol. 7, pp. 420–429, 1998, Abstract.

Scheuerle, A.F., "Diagnosis and follow–up in glaucoma patients using the Heidelberg retina tomograph" *Ophthalmologe,* vol. 100 pp. 5–12, 2003, Abstract.

Schneider, H. et al. "Transpupillary thermotherapy for malignant choroidal melanomas" *Ophthalmologe,* vol. 95, pp. 765–770, 1998, Abstract.

Schuman JS, et al. "Comparison of Optic Nerve Head Measurements obtained by Optical Coherence Tomography and Confocal Scanning Laser Ophthalmoscopy" Am J Ophthalmol 2003; 135: 504–512, Abstract.

Serguhn S, et al. "Can the Extent of Glaucoma damage be assessed by Measuring the Asymmetry of the Peripapillary Height Profile Between the Upper and Lower Retinal Half?" Klin Monatsbl Augenheilkd 1998; 212: 74–79, Abstract.

Sheen NJ, et al. "The effects of astigmatism and working distance on optic nerve head images using Heidelberg Retina Tomograph scanning laser Opthalmoscope." Am J Ophthalmol 2001; 131; 716–721, Abstract.

Sihota R, et al. "Variables Affecting Test–Retest Variability of Heidelberg Retina Tomograph II Stereometric Parameters." J Glaucoma 2002; 11: 321–328, Abstract.

Sihota, et al. "Correlation Between Confocal Scanning Laser Ophthalmoscopy and Scanning Laser Polarimetry in Open Angle Glaucoma." Eur J Ophthalmol 2003; 13: 266–275, Abstract.

Spaeth, et al. "The Disc Damage Liklihood Scale: Reproducibility of a New Method of Estimating the Amount of Optic Nerve Damage Caused by Glaucoma." Trans Am Ophthalmol Soc 2002; 100:181–185, Abstract.

Spencer AF, et al. "Vertical Optic Disk Diameter: Discrepancy Between Planimetric and SLO Measurements." Invest Ophthalmol Vis Sci 1995; 36:796–803, Abstract.

Spital G, et al. "Volume determination of pigment epthelium detachment in AMD by laser scanning tomography." Ophthalmologe 2000; 97: 173–180, Abstract.

Stave J, et al. "Modified Heidelberg Retinal Tomography HRT. Initial results of in vivo presentation of corneral structures." Ophthalmologe 2002; 99:276–280, Abstract.

Sugiyama K, et al. "The associations of optic disc hemorrhages with retinal nerve fiber layer defect and peripapillary atrophy in normal–tension glaucoma." Ophthalmology 1997; 104:1926–1933, Abstract.

Sung VCT, et al. "Agreement in assessing optic discs with a digital stereoscopic optic disc camera (Discam) and Heidelberg Retina Tomograph." Br J Ophthalmol 2002; 86:196–202, Abstract.

Swindale NV, et al. "Automated Analysis of normal and glaucomatous optic nerve head topography images" Invest Ophthalmol Vis Sci 2000; 41:1730–1742, Abstract.

Tamburrelli C, et al. "Ultrasonographic evaluation of Optic Disc Swelling: Comparison with CSLO in Idiopathic Intracranial Hypertension" Invest Ophthalmol Vis Sci 2000; 41:2960–2966, Abstract.

Tan JCH, et al. "Reasons for Rim Area Variability in Scanning Laser Tomography" Invest Ophthalmol Vis Sci 2003; 44:1126–1131, Abstract.

Tan JCH, et al. "Reference plane definition and reproducibility in optic nerve head images." Invest Ophthalmol Vis Sci 2003; 44:1132–1137, Abstract.

Tan, JCH, et al. "Variability across the optic nerve head in scanning laser tomography." Br J Ophthalmol 2003; 87:557–559, Abstract.

Tan JCH, et al. "Approach for Identifying Glaucomstous Optic Nerve Progression by Scanning Laser Tomography." Invest Ophthalmol Vis Sci 2003; 44:2621–2626, Abstract.

Teesalu, P. et al., "Correlation of blue–on–yellow visual fields with scanning confocal laser optic disc measurements". Invest Ophthalmol Vis Sci 1997; 38: 2452–2459, Abstract.

Teesalu, P. et al., "Hemifield association between blue–on–yellow visual field and optic nerve head topographic measurements". Graefes Arch Clin Exp Ophthalmol 1998; 236: 339–345, Abstract.

Thomson, S., "Retinal topography with the Heidelberg Retina Tomograph". J Audiov Media Med 1994; 17: 156–160, Abstract.

Tole, D.M., et al., "The correlation of the visual field with scanning laser opthalmoscope measurements in glaucoma." Eye 1998; 12: 686–690, Abstract.

Tomita, G., et al., "Reproducibilty of measurements by laser scanning tomography in eyes before and after pilocarpine treatment". Graefes Arch Exp Ophthalmol 1994; 252: 406–408, Abstract.

Tong, L., et al., "Sensitivity and specificity of a new scoring system for diabetic macular oedema detection using a confocal laser imaging system". Br J Ophthalmol 2001; 85: 34–39, Abstract.

Topouzis, F., et al., "Longitudinal changes in optic disc topography of adult patients after trabeculectomy". Ophthalmology 1999; 196: 1147–1151, Abstract.

Trick, G.L., et al.,"Quantitatived evaluation of papilledema in pseudotumor cerebri". Invest Ophthalmol Vis Sci 1998; 39: 1964–1971, Abstract.

Trick, G.L., et al., "Optic disc topography in pseudopapilledema: a comparasion to pseduotumor cerebri". J Neuro–Ophthalmol 2001; 21: 240–244, Abstract.

Tsai, C.S., et al., "Correlation of peripapillary retinal height and visual field in glaucoma and normal subjects". J Glaucoma 1995; 4: 110–116, Abstract.

Tsai, C.S., et al.,"Ethnic differences in optic nerve head topography", J Glaucoma 1995; 4: 248–257, Abstract.

Uchida H., et al., "Detection of structural damage from glaucoma with confocal laser image analysis". Invest Ophthalmol Vis Sci 1996; 37: 2393–2401, Abstract.

Uchida, H., et al., "Diagnostic capabilities of a classification program of the Heidelberg retina tomograph for early glaucomatous changes", Nippon Ganka Gakkai Zasshi 1998; 192: 333–339, Abstract.

Uchida, H., et al., "Peripapillary atrophy in primary angle-closure glaucoma: A comparative study with primary open-angle glaucoma". Am J Ophthalmol 1999; 127: 121–128, Abstract.

Uchida H., et al., "Clinical evaluation of the Heidelberg retina Tomograph II". Nippon Ganka Gakkai Zasshi 2000; 194: 826–829, Abstract.

Uchida H., et al., "Clinical evaluation of the Heidelberg retina Tomograph II", Jpn J Ophthalmol 2001; 45: 320, Abstract.

Ugurul S., et al., "Relationship between structural abnormalities and short–wavelength perimetric defects in eyes at risk of glaucoma". Am J Ophthalmol 2000; 129: 592–598, Abstract.

Verdonck N., et al., "Short–term intra–individual variability in Heidelberg Retina Tomograph II". Bull Soc Belge Ophthalmol 2002; 286: 51–57, Abstract.

Viestenz A., et al., "Vigabatrin–associated bilateral simple optic nerve atrophy with visual field construction. A case report and a survey of the literature". Ophthalmologe 2003; 100: 402–405, Abstract.

Vihanninjoki K., et al., "Comparison of optic disc measurements by Heidelberg Retina Tomograph and manual planimetric techniques". Acta Ophthalmol Scand 1997; 75: 512–515, Abstract.

Vihanninjoki K., et al., "Search for an optimal combination of structural and functional parameters for the diagnosis of glaucoma. Multivariate analysis of confocal scanning laser tomograph, blue–on–yellow visual field and retinal nerve fiber layer data". Graefas Arch Clin Exp Ophthalmol 2000; 238: 477–481, Abstract.

Vihanninjoki K., et al., "Optic disc biomorphometry with the Heidelberg Retina Tomograph at different reference levels". Acta Ophthalmol Scand 2002; 80: 47–53, Abstract.

Von der Lippe, I., et al., "Acute pressure–dependent change in the neuroretinal rim in juvenile glaucomatous papilla. Measurement with laser scanning tomography and planimetric biomorphometry". Klin Monatsbl Augenheilkd 1994; 194: 126–130, Abstract.

Watkins R., et al.,"Vertical cup–to–disc ratio: agreement between direct ophthalmoscopic estimation, fundus biomicroscopic estimation, and scanning laser ophthalmoscopic measurement", Optom Vis Sci 2003; 80: 454–459, Abstract.

Weinberger D., et al., "Three–dimensional measurements of idiopathic macular holes using scanning laser tomography". Ophthalmology 1995; 102: 1445–1449, Abstract.

Weinberger D., et al., "Three–dimensional measurements of central serous chorioretinopathy using a scanning laser tomograph". Am j Ophthalmol 1996; 122: 864–869, Abstract.

Weinreb R.N., "Laser scanning tomography to diagnose and monitor glaucoma". Curr Opin Ophthalmol 1993; 4: 3–6, Abstract.

Weinreb, R.N., et al.,"Effect of repetitive imaging on topographic measurements of the optic nerve head", Arch Ophthalmol 1993; 111: 636–638, Abstract.

Weinreb R.N., et al., "Association between quantitative nerve fiber layer measurement and visual field in glaucoma". Am J Ophthalmol 1995; 120: 732–738, Abstract.

Weinreb R.N., "Imaging technologies for assessing neuroprotection in glaucomatous optic neuropathy". Eur J Ophthalmol 1999; 9. Suppl 1: S40–S43, Abstract.

Wollstein G., et al., "Identification of early glaucoma cases with the scanning laser ophthalmoscope". Ophthalmology 1998; 195: 1557–1563, Abstract.

Wollstein G., et al., "Glaucomatous optic disc changes in the contralateral eyes of unilateral normal pressure glaucoma patients", Ophthalmology 2000; 107: 2267–2271, Abstract.

Wollstein G., et al., "Identifying early glaucomatous changes: Comparison between expert clinical assessment of optic disc photographs and confocal scanning ophthalmoscopy". Ophthalmology 2000; 107: 2272–2277, Abstract.

Wu, L.L., et al., "Frequency doubling technology and confocal scanning ophthalmoscopic optic disc analysis is open–angle glaucoma with hemifield defects". J Glaucoma 2001; 10: 256–260, Abstract.

Wu, L., et al., "Evaluation of optic disc in open–angle glaucoma with hemifield defect by Heidelberg retinal tomography", Chung Hua Yen Ko Tsa Chih 2001; 37: 414–417, Abstract.

Wu, L., et al., "Frequency–doubling perimetry in examination of open–angle glaucoma with hemifield defect". Chung Hua Yen Ko Tsa Chih 2002; 38: 717–720, Abstract.

Yamagishi N., et al., "Mapping structural damage of the optic disk to visual field defect in glaucoma". Am J Ophthalmol 1997; 123: 667–676, Abstract.

Yamazaki Y., et al., "Influence of myopic disc shape in a classification program of the Heidelberg retina tomograph". Nippon Ganka Gakkai Zasshi 1999; 103: 392–398, Abstract.

Yamazaki Y., et al., "Influence of myopic disc shape on the diagnostic precision of the Heidelberg Retina Tomograph". Jpn J Ophthalmol 1999; 43: 393–397, Abstract.

Yamazaki Y., et al., "Correlation between blue chromatic macular sensitivity and optic disc change in early glaucoma patients". Nippon Ganka Gakkai Zasshi 2001; 195: 776–800, Abstract.

Yamazaki Y, et al., "Correlation of blue chromatic macular sensitivity with optic disc change in early glaucoma patients". Jpn J Ophthalmol 2002; 46: 89–94, Abstract.

Yan, D.B., et al., "Study of regional deformation of the optic nerve head using scanning laser tomogrpahy". Curr Eye Res 1998; 17: 903–916, Abstract.

Yang, J.G., "A comparison of optic nerve head topography in primary open–angle glaucoma and normal–tension glaucoma in Korean". Korean J Ophthalmol 1997; 11: 79–83, Abstract.

Yoshida A., "New examination method for macular disorders—application of diagnosis and treatment". Nippon Ganka Gakkai Zasshi 2000; 104: 899–942, Abstract.

Yoshida A., "New examination methods for macular disorders. Application of diagnosis and treatment". Jpn J Ophthalmol 2001; 45: 323–324, Abstract.

Yoshikawa K., et al., "Reproducibility of the topographic parameters of the optic disk with the scanning laser tomograph". Nippon Ganka Gakkai Zasshi 1995; 99: 469–474, Abstract.

Yoshikawa K., et al., "Changes in optic disc parameters after intraocular pressure reduction in adult glaucoma patients". Jpn J Ophthalmol 1999; 43: 225–231, Abstract.

Yoshikawa K., et al., "Stereometry of temporal peripillary atrophy in early–stage open–angle glaucoma". Nippon Ganka Gakkai Zasshi 1999; 103: 538–543, Abstract.

Yucel, Y.H., et al., "Relationship of optic disc topography to optic nerve fiber number in glaucoma". Arch Ophthalmol 1998; 116: 493–497, Abstract.

Zambarakji H.J., et al, "Volumetric analysis of early macular edema with the Heidelberg Retina Tomograph in diabetic retinopathy". Ophthalmology 1998; 195: 1051–1059, Abstract.

Zambarakji H.J., et al., "Reproducibility of volumetric measurements of normal maculae with the Heidelberg Retina Tomograph". Br J Ophthalmol 1998; 82: 884–891, Abstract.

Zambarakji H.J., et al., "Assessment of the Heidelberg Retina Tomograph in the detection of sight–threatening diabetic maculopathy", Eye 1999; 13: 136–144, Abstract.

Zambarakji H.J., et al., "Reproducibility of volumetric macular measurements in diabetic patients with the Heidelberg Retina Tomograph". Doc Ophthalmol 1999; 97: 349–360, Abstract.

Zangwill L., et al., "Agreement between clinicians and a confocal scanning laser ophthalmoscope in estimating cup-disc ratios". Am J Ophthalmol 1995; 199: 415–421, Abstract.

Zangwill L., et al., "Optic nerve topography in ocular hypertensive eyes using confocal scanning laser ophthalmoscopy". Am J Ophthalmol 1996; 122: 520–525, Abstract.

Zangwill L., et al., "effect of cataract and pupil size on image quality with confocal scanning laser ophthalmoscopy". Arch Ophthalmol 1997; 115: 983–990, Abstract.

Zangwill L.M., et al., "Optic disc topographic measurements after pupil dilation". Ophthalmology 1999; 106; 1751–1755, Abstract.

Zangwill L.M., et al., "New technologies for diagnosing and monitoring glaucomatous optic neuropathy". Optom Vis Sci 1999; 76: 526–536, Abstract.

Zangwill L.M., et al., "Discriminating between normal and glaucomatous eyes using the Heidelberg retina Tomograph, GDx Nerve Fiber Analyzer, and Optical Coherence Tomograph". Arch Ophthalmol 2001; 119: 985–993, Abstract.

Zinser G., "Topographic measurements at the fundus with the Heidelberg retina Tomograph", Kampik A, ed., Jarhbuch der Augenheilkunde 1992, Laser, Beirmann, Zulpich, pp. 175–180, 1992, Abstract.

Zinser G., "Topographic measurements at the fundus with the Heidelberg Retina Tomograph". Jpn J Vis Sci 1992; 13: 237–249, Abstract.

* cited by examiner

THREE DIMENSIONAL REAL-TIME IMAGE APPARATUS OF OCULAR RETINA

FIELD OF THE INVENTION

The present invention relates to a three dimensional real time apparatus for imaging an ocular retina and more specifically to a three dimensional real-time apparatus for imaging an ocular retina wherein the optical system is so arranged that, with reference to the retina, the incident angles of the laser beams irradiated on the retina at respective moments and the output angles of imaginary or extended lines of the same laser beams reflected from the retina may agree with each other in both the vertical and horizontal direction to allow three dimensional real-time observation for the retina.

BACKGROUND OF THE INVENTION

The eyeball mainly consists of a crystalline lens, retinal, glass body, sclera, cornea and the like. The retina of them is a thin and almost transparent membrane of three-dimensional structure with the thickness of 170$\mu$ to 500$\mu$ and particularly it can become somewhat thicker or thinner due to retinal edema under a pathologic condition. Currently two dimensional image of retina is used for diagnosis and treatment. However, in order to clarify pathological retinal phenomena and observe the dynamic changes, real-time three dimensional image scanning of the retina is needed. Nevertheless, it is true that no satisfactory image technology has been developed so far.

The equipments currently available, which allow for approximate three dimensional image of the retina at least partially, may be mentioned as follows:

First, there is a RTA(Retina Thickness Analyzer). This RTA apparatus scans the cross sections of the retina, wherein the distance between the light reflecting on the front of a retina and that reflecting on the back of the retina is analyzed, so that the thickness of the retina may be represented as in contour lines in a map. These equipments are defective, however, in that these simply show the vertical irregularities of a retina by using lines based on non-real time scanning, without permitting a practical observation of the retina.

Second, the SLO(Scanning Laser Ophthalmoscope) has also been developed. This equipment is a two dimensional retinal imaging apparatus based on real time scanning lines by irradiating laser ray on one point of a retina at an instant to form the corresponding image on a monitor. This equipment is also problematic because this does not permit three dimensional real-time observation of a retinal image as well.

Third, the OCT(Optical Coherence Tomography) is also available. This OCT apparatus realizes a high resolution in representing the cross sections of a retina in the form of lines. Similarly, this equipment is not operated on real-time scanning and can not provide three dimensional image beside the retinal cross section on a certain line.

Fourth, the HRT(Heidelberg Retinal Tomography) is also available. This equipment is not also based on the real-time scanning and further has the problem of simply representing overall retinal irregularities in the form of grids.

SUMMARY OF THE INVENTION

Therefore, the object of the invention, in consideration of the above-described drawbacks with the conventional arts, is to provide a three dimensional real-time apparatus for imaging ocular retina wherein the optical system is so arranged that, with reference to the retina, the incident angle of the laser beams irradiated on the retina at respective moments and the output angles (radiation angle) of imaginary or extended lines of the laser beams reflected from the retina may agree with each other in both the vertical and horizontal direction to allow three dimensional real-time observation for the retina.

The above object is achieved according to the invention by a three dimensional real-time apparatus for imaging an ocular retina which comprises a laser generating device for generating laser beams, an optical means for making the output angles of imaginary or extended lines of the laser rays reflected from the retina agree with the incident angles of the same laser beams irradiated on the retina at respective moments in both the vertical and horizontal direction and a three dimensional imaging means for converting the image of the retina extracted from the optical means to a real-time three dimensional image.

DETAILED DESCTIPRION OF THE INVENTION

A preferred embodiment of the invention will be described in detail below by referring to the accompanying drawings.

Figure 1:
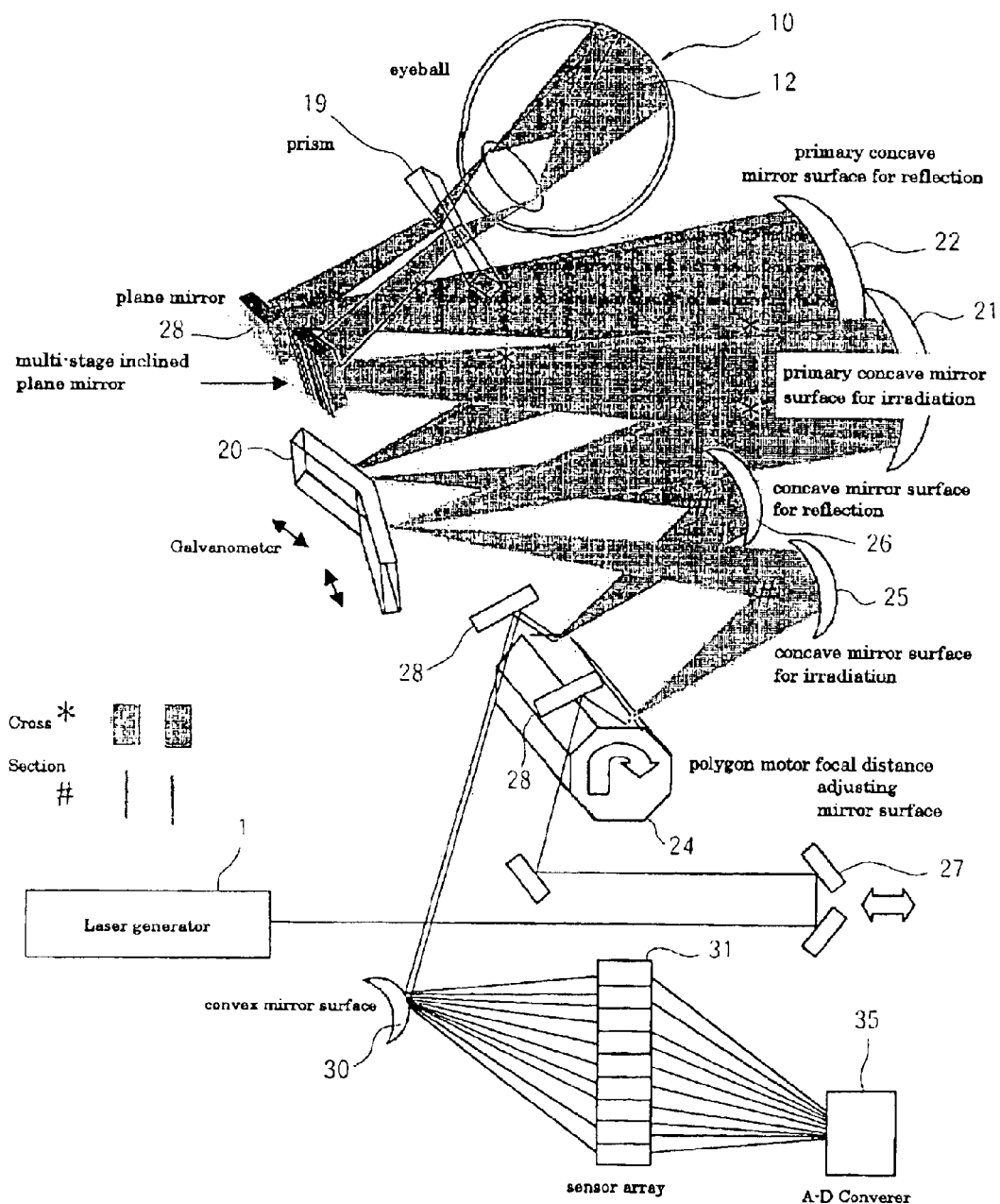
FIG. 1 shows the schematic view of arrangement for the optical system of three dimensional real-time retina imaging apparatus according to the invention.

FIG. 1 shows the schematic view of arrangement for the device according to the invention.

The laser generator 1 emits laser beams to take the image of the retina 12 of an eyeball 10. The laser beam emitted from the laser generator 1 is irradiated on a right-angled plane mirror 27 for controlling the focus of laser beam. The right-angled plane mirror 27 for controlling the focus of laser beam functions to control the focal distance of the laser beam irradiated on the retina 12 by controlling the distance from the laser generator 1. The beam which has passed the plane mirror 27 is irradiated on a polygon motor 24 via a plane mirror 28. The polygon motor 24 is in the form of a polygon, with each face of polygon forming a mirror. The polygon motor 24 rotates around its axis with time in a fixed direction so that the laser beam irradiated from the plane mirror 28 may be scanned up and down. The scanned laser beams from the polygon mirror 24 are irradiated to one mirror surface of a galvanometer 20 by way of a mirror surface 25 for irradiating laser beams. The galvanometer 20 is composed of two mirrors which are linked around a contact line at a finite angle. This galvanometer 20 functions to sequentially form two dimensional beam surface with time by scanning left and right the laser beams irradiated from the polygon motor 24. The two dimensional laser beams formed by the galvanometer 20 are applied to a prism 19 through a primary mirror surface 21 for laser irradiation. The prism 19 focuses and irradiates the laser beam irradiated thereon onto the retina 12 and the monochromic rays irradiated on the retina are reflected back through the prism 19. At this time, it is found that the incidence angles of the laser beams irradiated on the retina 12 and the reflection angles of the laser beams reflected on the retina 12 agree with each other within a certain angle in both the vertical and horizontal direction, as if the retina acted as an ideal reflector. The reflected laser beams which have been refracted by means of the prism 19 are reflected, now as imaginary or extended reflected rays, on a primary mirror surface 22 for reflected rays and then irradiated again on the other mirror surface of the galvanometer 20. The reflected imaginary laser rays irradiated on the galvanometer 20 are applied on the polygon mirror motor 24 via a second mirror surface 26 for reflected rays. It is so arranged that the current reflected imaginary laser rays are irradiated on the same surface of plural mirror surfaces that previously engaged with the laser beam irradiated from the plane mirror 101. Moreover, the laser beam irradiated on the polygon mirror motor 24 and the reflected imaginary laser ray on the same mirror motor are preferably caused to position at a finite spacing. Subsequently the laser single line output from the polygon motor 24 is irradiated on a convex mirror surface 30 via plane mirror 101. The convex mirror surface 30 serves to eject and distribute the series of laser single lines at correct output angles onto a sensor array 31, 50 that the sequential laser single lines reflected on the retina may match the array of sensors 31. The laser single lines output from the sensor array 31 are applied to an A/D converter 35. Thanks to such an arrangement of optical system, the relation of the same output angle of the imaginary rays reaching the array of sensors 31 from the reflecting point ahead of the sensor array as the incident angle of the laser beams irradiated on a retina 12 is maintained.

Figure 2:
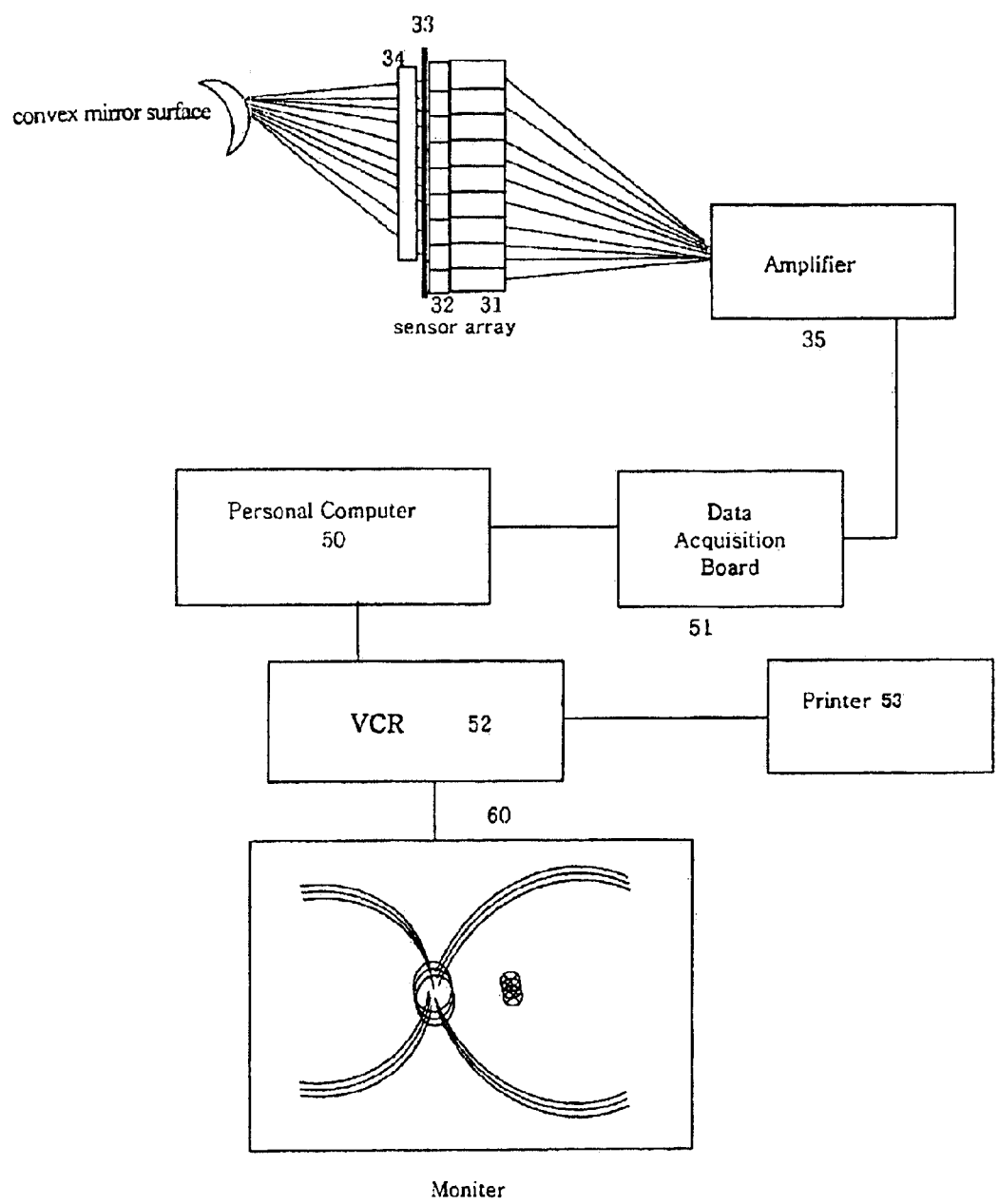
FIG. 2 shows a schematic view of arrangement for the sensor array according to the invention.

FIG. 2 shows the schematic arrangement for the sensor array according to the invention.

The laser single lines which have passed the convex mirror surface 30 as described in conjunction with FIG. 1 are distributed over the sensor array 31. The front side of the sensor array 31 is provided with a co-focus filter 34 which blocks the component of scattered beams out of the laser single rays input from the convex mirror surface 30 and receives only the component of reflected beams. On the rear side of co-focus filter 34 there is provided a grid filter 33 which functions to receive only the component of vertically incident laser beams out of the laser single lines from the co-focus filter 34. Further, on the rear side of the grid filer 33, there is provided a section dividing convex lens 32 to apply the laser single lines from the filter 33 dividedly to the sensor array 31. Therefore, the sequential single rays at the retina 12 can be separated with a high resolution. The laser single lines which have passed the sensor array are applied to the A/D converter 35.

Figure 3A:
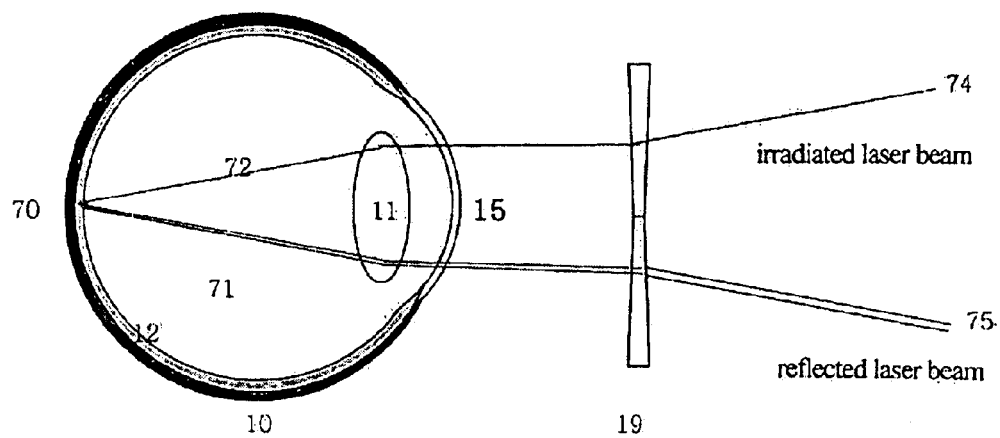
FIGS. 3a and 3b show the views illustrating the horizontal and vertical reflection of the laser rays lit on the retina in the eyeball and retinal single rays, according to the invention.

FIG. 3a shows the view of the horizontal reflection of the laser beams lit on the retina in an eyeball and the retinal single rays.

As shown in FIG. 3a, the laser irradiating rays 74 outside an eyeball are irradiated on the cornea 15 of an eyeball 10 through the prism 19. The laser beams pass the crystalline body 11 following the cornea 15 to be irradiated on the retina 12 by means of the laser irradiating rays 72 in the eyeball. The numeral 70 stands for the area where laser single lines at the retina 12 perform scanning. The reflected imaginary rays 71 reflected on the retina 12 within the eyeball lead to the reflected imaginary laser rays 75 outside the eyeball through the prism 19. At this time, the arrangement should be so adjusted that even the laser rays irradiated on the areas near the left and right boundaries of the enlarged pupil and the corresponding reflected imaginary rays may illuminate the same points within the retina 12, with the focuses of incident and reflected rays agreeing with each other. Accordingly, the horizontal angles of the respective laser rays irradiated on the retina 12 and the horizontal output angles of the same imaginary rays orienting toward the array of sensors 31, which imaginary rays have the same origin as the light reflected at the retina now under consideration of comparison, are ensured to be maintained the same, so that the real-time three dimensional retinal imaging can be realized.

Figure 3B:
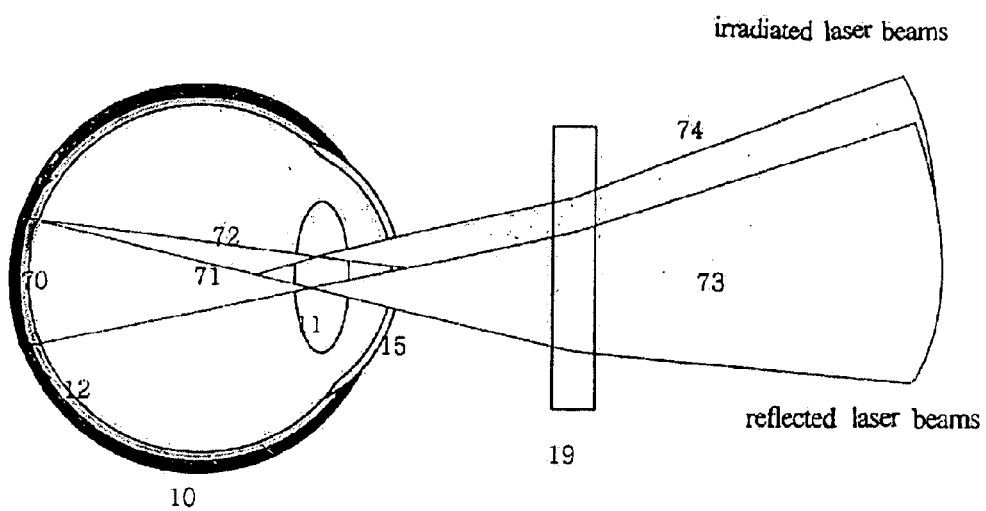

FIG. 3b shows the view of the vertical reflection of the laser beams lit on the retina in an eyeball and the retinal single rays.

As shown in FIG. 3b, the laser irradiating rays 74 outside an eyeball are irradiated on the retina 12 through the prism 19. The reflected imaginary rays reflected from the retina 12 form the reflected imaginary laser rays 73 outside the eyeball through the prism 19. At this time, the arrangement should be so adjusted that even the laser rays irradiated on the areas near the opposite boundaries of the enlarged pupil and the corresponding reflected imaginary rays may illuminate the same points within the retina 12, with the focuses of incident and reflected rays agreeing with each other. Accordingly, the vertical angles of the respective laser rays irradiated on the retina 12 and the vertical output angles of the same-origin corresponding imaginary rays received on the array of sensors 31 are ensured to be maintained the same, so that the real-time three dimensional retinal imaging can be realized.

Figure 4A:
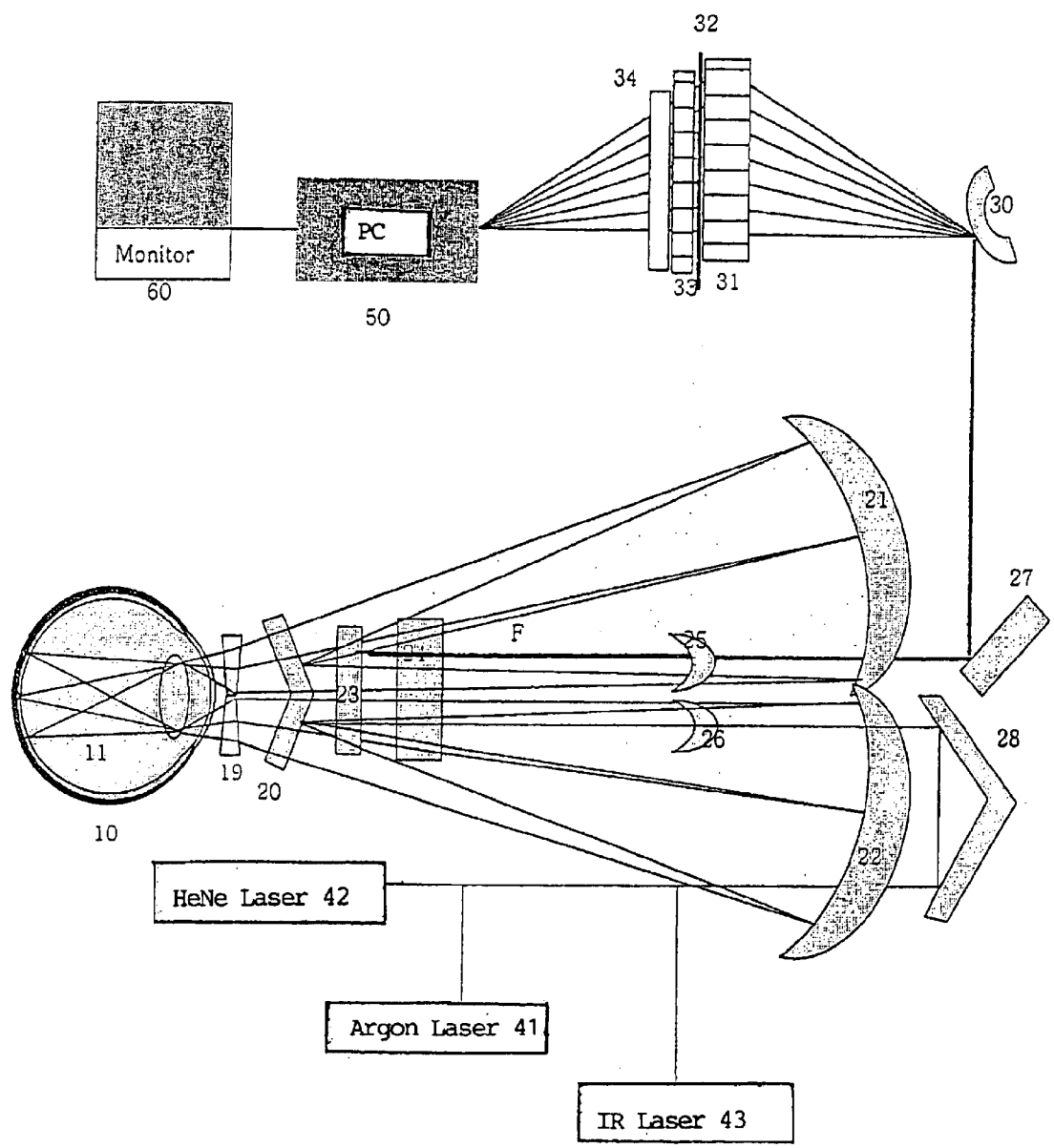
FIGS. 4a and 4b show the plan and side view for three dimensional real-time retina imaging apparatus according to the invention.
Figure 4B:
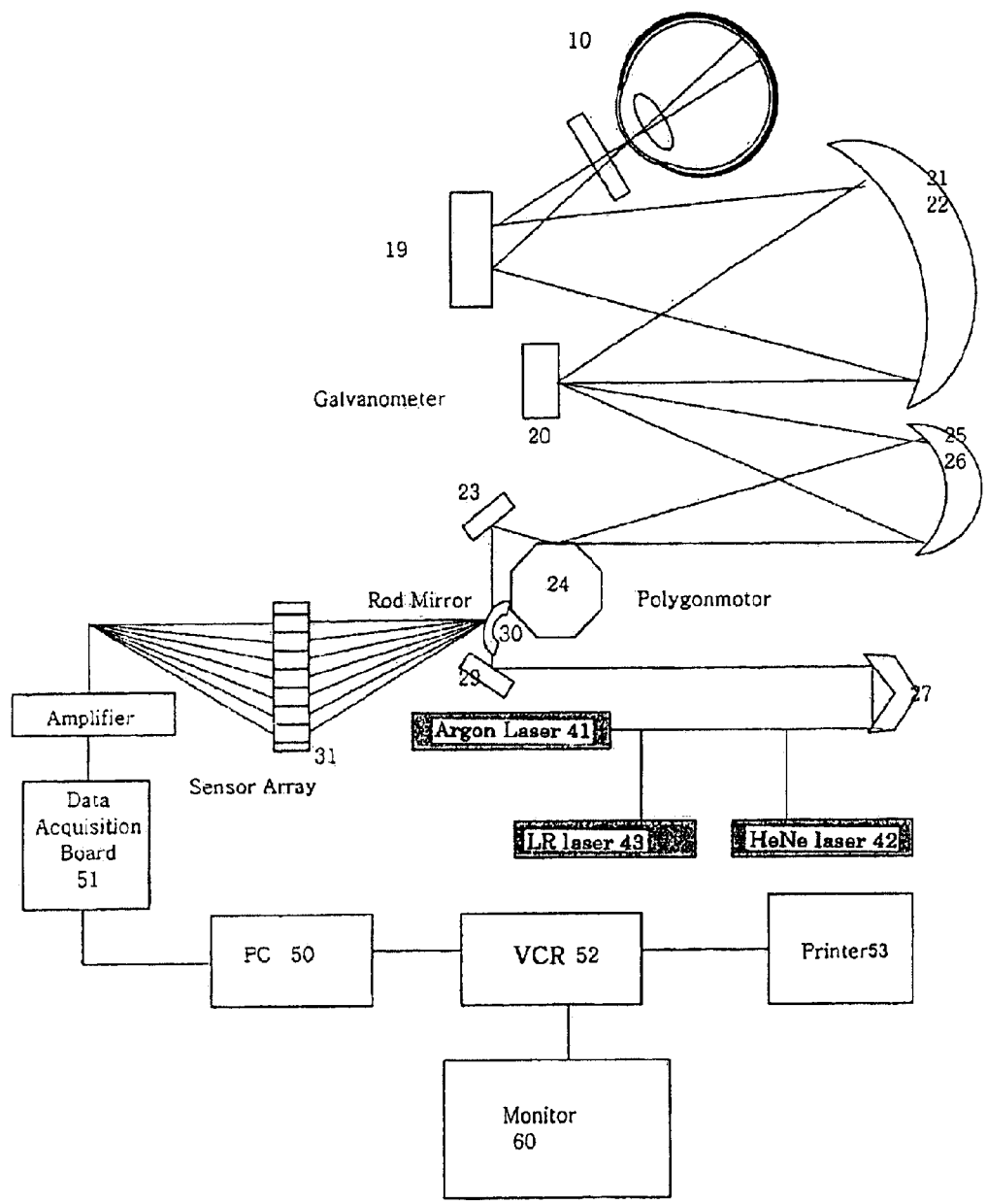

FIGS. 4a and 4b show the plan and elevation view for the three dimensional real-time retina imaging device according to the invention, wherein the incident angle of the laser rays irradiated to the retina 12 and the output angle of same-origin reflected imaginary rays are maintained the same to prevent the deflection of the laser beams and the reflected imaginary rays. In order for the irradiated rays and the imaginary rays based on the reflected rays to be in agreement, two rows of arrangements up to the primary mirror surfaces for laser irradiation/reflection 21 and 22 are lined up on both sides of the central line passing through the retina 12 as the apex, forming a finite angle therebetween, as seen in FIG. a.

On the other hand, the laser generator 1 may be composed as a helium neon (HeNe) laser 42, argon (Ar) laser 41 or infrared laser 43. The laser beams emitted from the laser generator 1 is irradiated on a right-angled plane mirror 27. The beam which has passed the plane mirror 27 is irradiated on a polygon motor 24 via a plane mirror 28. The polygon motor 24 scans the irradiated laser beams upward and downward with the lapse of time before supplying to the second mirror surfaces 25 for laser irradiation. The laser beams from the second mirror surface 25 are irradiated to a galvanometer 20, which form laser cross sections by scanning left and right the laser beams. The laser cross sections supplied from the galvanometer 20 are irradiated on the retina 12 via the primary mirror surface 21 and then through the prism 19. The reflected imaginary laser rays reflected from the retina 12 are reflected on the convex mirror surface 30 after going through the galvanometer 20 and polygon mirror motor 24. The arrangement of the optical system corresponding to the description just mentioned is the same as in the description for FIG. 1. Next, the laser single lines from the convex mirror surface 30 are distributed on the sensor array in agreement with it. The analog data signals output from the sensor array 31 are input in the A/D converter 35 to be converted in digital data. The respective rays corresponding to sequentially reflected laser beams at the retina 12 are converted into digital signals and supplied to a visual board 51. The converted digital data signals are input into the visual board 51, where signal processing is conducted to apply the image of the retina to a PC 50. The PC 50 receives signal-processed image data from the visual board 51 and images the same number of two dimensional surface elements as the number of sensors of the sensor array 31 as real time three dimensional images. The PC 50 recognizes the single rays lit on respective points of the retina 12 at respective moments as sequential signal values of monitor output to produce three dimensional real-time images. In other words, data successively input at the same time from the sensor array 31 are spread to corresponding points as in a SLO apparatus to get planar images of the retina 12 and further analyzing the rate of change in neighboring data at respective moments can lead to three dimensional real time image. The three dimensional images so generated may be recorded/reproduced through a VCR 52 or output through a printer 53. Further, a user can observe three dimensional real-time images for the retina by displaying through a monitor 60.

Figure 5A:
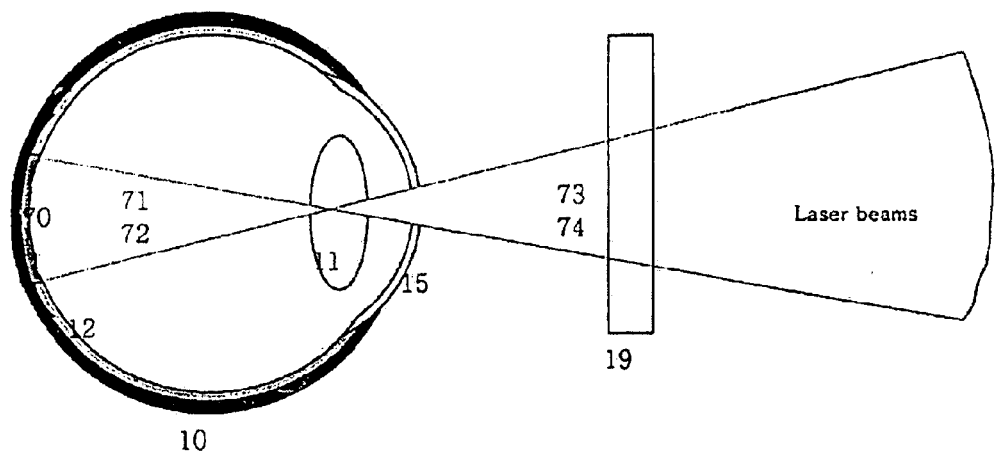
FIGS. 5a to 5c show the views illustrating the direction of laser beams within the eyeball according to the invention.
Figure 5B:
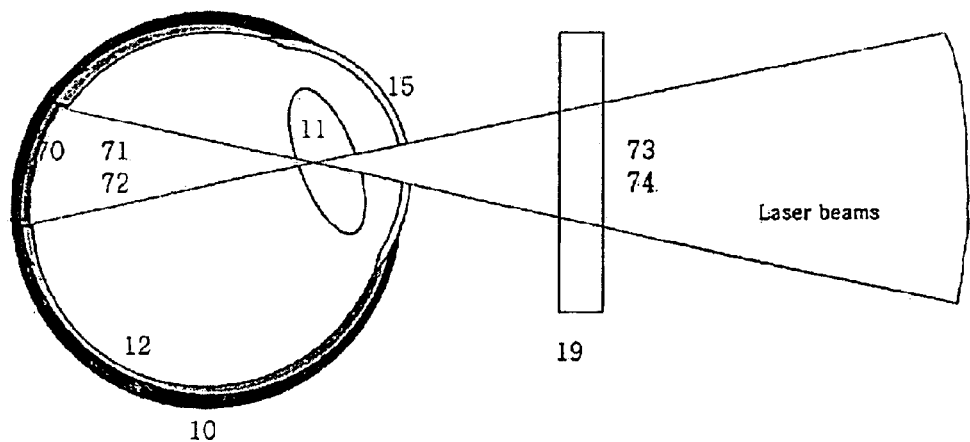
Figure 5C:
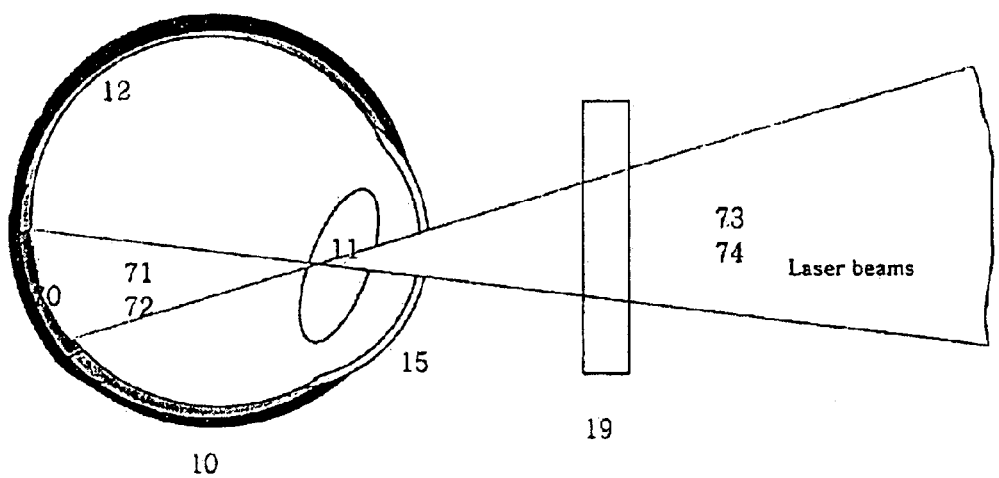

FIGS. 5a to 5c show the views showing the direction of laser beams inside an eyeball according to the present invention. FIG. 5a shows the irradiating direction of laser beams inside an eyeball for the case of scanning the central part of eye-ground, FIG. 5b relates to the case of scanning the upper part of eye-ground, and FIG. 5c relates to the case of scanning the lower part of eye-ground.

Figure 6A:
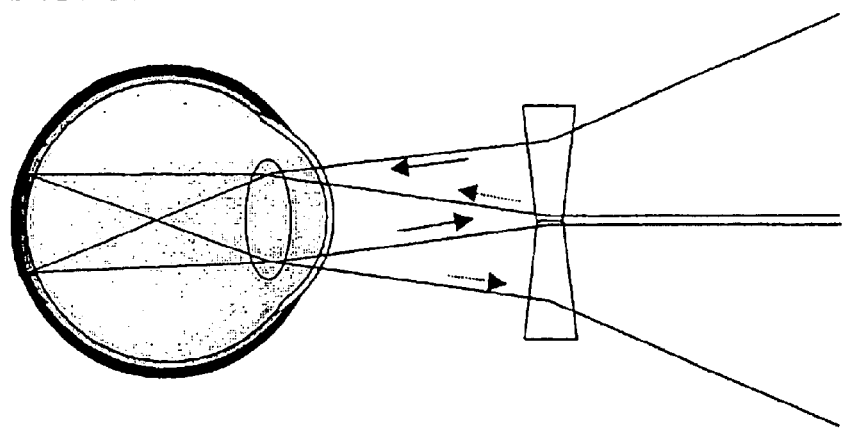
FIGS. 6a to 6c show the views for illustrating the laser scanning beams and reflected imaginary lines for the emmetropia, myopia and hypermetropia.
Figure 6B:
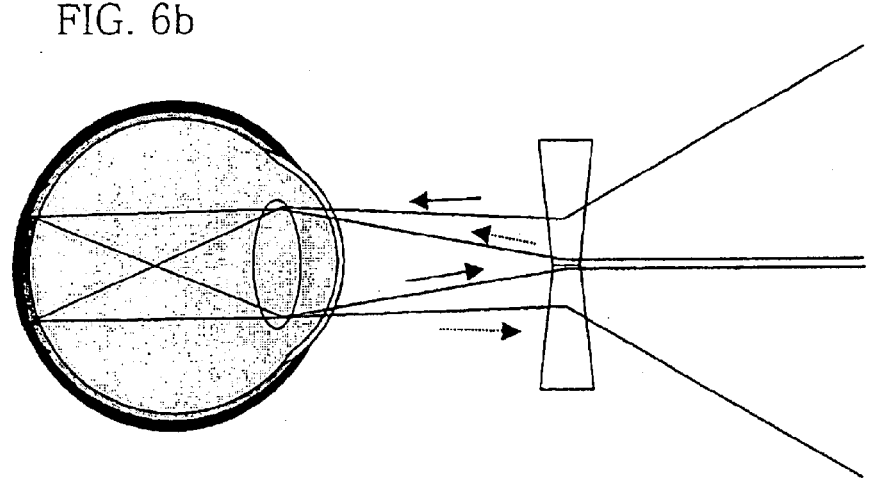
Figure 6C:
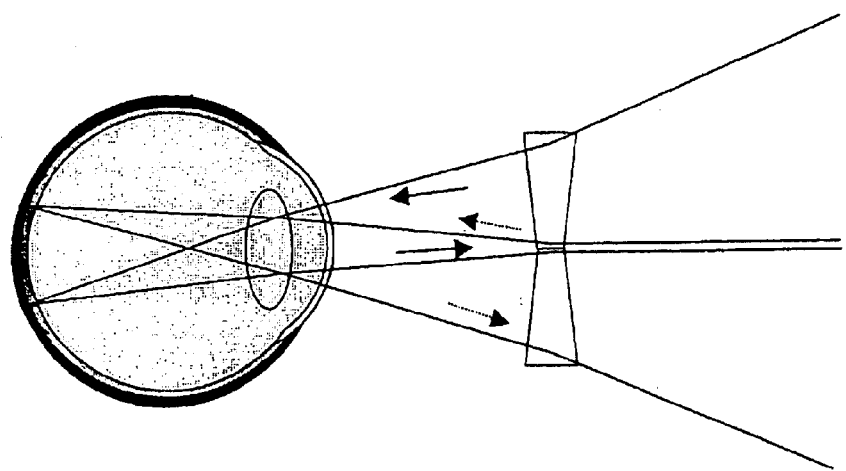

FIGS. 6a to 6c show the views illustrating the laser scanning beams and reflected imaginary rays for the case of emmetropic eye, myopic eye and hypermetropic eye.

The retinal surface is not a plane but a spheric surface with the center of curvature located at the center of eyeball. Therefore, for the case of emmetropia, the optical system is so adjusted that the incident laser ray and the corresponding extended reflected ray at the position behind the prism and before the eye may run parallel, as seen in FIG. 6a. For the case of myopia, the incident laser ray and the relevant extended reflected ray at the position behind the prism and before the eye should run tapering toward the prism, as seen in FIG. 6b. On the other hand, for the case of hypermetropia, the irradiated laser ray to the eye and the relevant extended reflected ray from the eye should run tapering toward the eye, as seen in FIG. 6c.

Figure 7A:
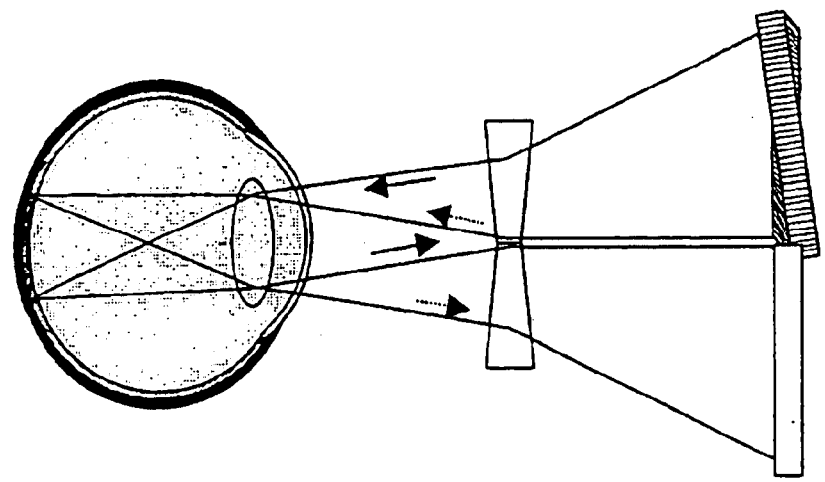
FIGS. 7a and 7b show the plan and side view for the prism and the plane mirror composed of multiple individual inclined mirrors, positioned in front of an eye.
Figure 7B:
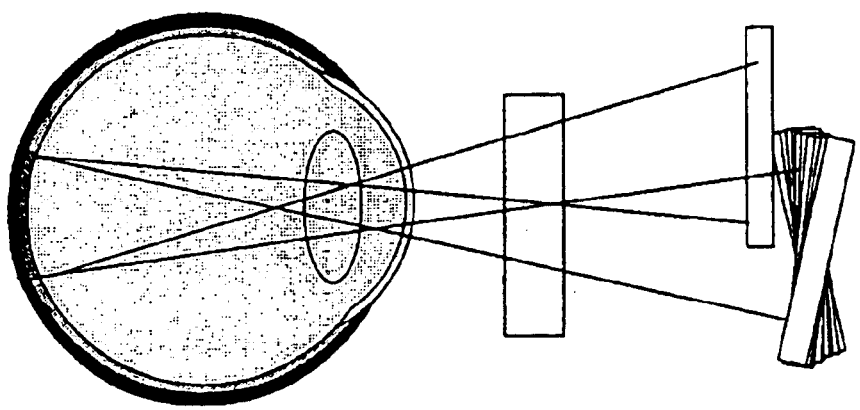

The distortion of image resulting in the course of guiding the light to the eyeball from the primary mirror surface which is inclined causes the direction of the retinal vertical scanning and the direction of scanning by a detector to mismatch but to cross each other. To compensate for such a disagreement in the scanning of the laser ray lit on the retina and the retinal reflected ray the plane mirror positioned in front of the eyeball is formed of multiple plane mirrors which are stepwise inclined toward the relevant irradiated laser rays, as shown in FIGS. 7a and 7b.

As described above, the prism 19 takes part in causing the incident angle of the laser beams irradiated on the retina to correspond to the output angle of the reflected imaginary lines by adjusting the entering angle of laser beams and the leaving angle of the reflected imaginary lines through the prism.

As described in the above, the three dimensional real-time retina imaging apparatus according to the invention permits three dimensional inspection of eye-ground, sensitive imaging of various retinal diseases and detailed evaluation of the responses to various treatments, so that it can give an epochal assistance to the understanding of retinal diseases and the development of the therapeutic methods.

It is to be understood that, while the invention was described only with respect to a preferred embodiment, the invention is never restricted to that embodiment and a variety of modifications and alterations would be possible to a man skilled in the art by referring to the description or drawings presented here and within the spirit of the invention and thus those modifications or alterations are to fall within the scope of the invention, which scope should be limited only by the attached claims.

What is claimed is:

1. A three dimensional real-time apparatus for imaging an ocular retina which comprises:

a laser generating device for generating laser beams;

an optical means for causing the incident angles, relative to a retina, of the laser beams irradiated on the retina at respective moments to agree with the output angles of imaginary lines of the same laser beams reflected from the retina in both the vertical and horizontal direction; and a three dimensional imaging means for converting images of the retina extracted from the optical means to real-time three dimensional images, wherein said optical means comprises:

a polygon motor having plural mirror surfaces for vertically scanning the laser beams emitted from the laser generating device through rotating operation;

a galvanometer for producing parallel rays by laterally scanning the laser beams from the polygon motor and for irradiating the parallel rays so produced to the galvanometer;

and an array of sensors arranged in such a manner that laser single rays can be applied thereto at predetermined inclined angles, said laser single rays having passed the galvanometer and the polygon motor after their reflection on the retina, wherein said optical means further comprises a convex mirror surface for applying the laser single rays from the polygon motor, in a distributed manner, to the sensor array in such a manner that the output angles of rays reflected from the convex mirror surface have the same angles as the incident angles of the laser beams at the retina as the laser single rays from the polygon motor.

2. A three dimensional real-time apparatus for imaging an ocular retina which comprises:

a laser generating device for generating laser beams;

an optical means for causing the incident angles, relative to a retina, of the laser beams irradiated on the retina at respective moments to agree with the output angles of imaginary lines of the same laser beams reflected from the retina in both the vertical and horizontal direction; and a three dimensional imaging means for converting images of the retina extracted from the optical means to a real-time three dimensional images, wherein said optical means comprises:

a polygon motor having plural mirror surfaces for vertically scanning the laser beams emitted from the laser generating device through rotating operation;

a galvanometer for producing parallel rays by laterally scanning the laser beams from the polygon motor and for irradiating the parallel rays so produced to the galvanometer;

and an array of sensors arranged in such a manner that laser single rays can be applied thereto at predetermined inclined angles, said laser single rays having passed the galvanometer and the polygon motor after their reflection on the retina, wherein said sensor array further comprises:

a co-focus filter for blocking the scattered beams out of the laser single rays input from a convex mirror surface and for receiving only the reflected beams;

a grid filter for receiving only the vertically incident laser beams out of laser single lines from the co-focus filter; and a section dividing convex lens for applying the laser single lines from the grid filter dividedly to the sensor array.

3. A three dimensional real-time apparatus for imaging an ocular retina which comprises:

a laser generating device for generating laser beams;

an optical means for causing the incident angles, relative to a retina, of the laser beams irradiated on the retina at respective moments to agree with the output angles of imaginary lines of the same laser beams reflected from the retina in both the vertical and horizontal direction; and a three dimensional imaging means for converting images of the retina extracted from the optical means to real-time three dimensional images, wherein said optical means comprises:

a polygon motor having plural mirror surfaces for vertically scanning the laser beams emitted from the laser generating device through rotating operation;

a galvanometer for producing parallel rays by laterally scanning the laser beams from the polygon motor and for irradiating the parallel rays so produced to the galvanometer;

and an array of sensors arranged in such a manner that laser single rays can be applied thereto at predetermined inclined angles, said laser single rays having passed the galvanometer and the polygon motor after their reflection on the retina, wherein arrangement is made in such a manner that an incident laser ray and a relevant reflected laser imaginary line at a position between a prism and an eye may run parallel, for the case of emmetropia, the incident laser ray and the relevant reflected laser imaginary line may run tapering together toward the prism, for the case of myopia, and the incident laser ray and the relevant reflected laser imaginary line may run tapering together toward the eye, for the case of hypermetropia.

* * * * *